United States Patent
Dickie et al.

(10) Patent No.: US 12,251,267 B2
(45) Date of Patent: Mar. 18, 2025

(54) METHOD AND SYSTEM FOR IDENTIFYING A TENDON IN ULTRASOUND IMAGING DATA AND VERIFYING SUCH IDENTITY IN LIVE DEPLOYMENT

(71) Applicant: Clarius Mobile Health Corp., Vancouver (CA)

(72) Inventors: Kris Dickie, Vancouver (CA); Nishant Uniyal, Vancouver (CA); Parisa Asgharzadeh, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 8 days.

(21) Appl. No.: 17/359,453

(22) Filed: Jun. 25, 2021

(65) Prior Publication Data
US 2022/0409181 A1   Dec. 29, 2022

(51) Int. Cl.
*A61B 8/00* (2006.01)
*A61B 8/08* (2006.01)
*G06N 3/047* (2023.01)
*G06N 3/08* (2023.01)

(52) U.S. Cl.
CPC .............. *A61B 8/5207* (2013.01); *A61B 8/08* (2013.01); *A61B 8/461* (2013.01); *A61B 8/468* (2013.01); *G06N 3/047* (2023.01); *G06N 3/08* (2013.01); *G06V 2201/03* (2022.01)

(58) Field of Classification Search
CPC ......... A61B 8/5207; A61B 8/08; A61B 8/461; A61B 8/468; A61B 8/085; A61B 8/5223; A61B 8/565; G06N 3/0472; G06N 3/08; G06N 3/047; G06N 3/0464; G06N 3/09; G06V 2201/03
See application file for complete search history.

(56) References Cited

U.S. PATENT DOCUMENTS

| | | | |
|---|---|---|---|
| 2017/0055938 A1* | 3/2017 | Krasnow | A61B 8/4227 |
| 2020/0046324 A1* | 2/2020 | Veronesi | G06T 7/40 |
| 2020/0100763 A1* | 4/2020 | Noguchi | A61B 8/54 |

(Continued)

FOREIGN PATENT DOCUMENTS

WO   WO-2020185455 A2 *   9/2020   ........... A61B 5/4523

OTHER PUBLICATIONS

Gupta, R., Elamvazuthi, I., Dass, S.C. et al. Curvelet based automatic segmentation of supraspinatus tendon from ultrasound image: a focused assistive diagnostic method. BioMed Eng OnLine 13, 157 (2014). https://doi.org/10.1186/1475-925X-13-157 (Year: 2014).*

(Continued)

*Primary Examiner* — Joel Lamprecht
*Assistant Examiner* — James F McDonald, III
(74) *Attorney, Agent, or Firm* — Julian Ho; Susan Ben-Oliel

(57) ABSTRACT

A method and system provide for the identification of a tendon in ultrasound imaging data, by deploying an artificial intelligence (AI) model to execute on a computing device, wherein the AI model is trained to identify a plurality of different types of tendons imaged in ultrasound imaging data, and when deployed, the computing device generates a probability for each of the plurality of different types of tendons that the type of tendon is imaged in new ultrasound imaging data and wherein such probability is corroborated by at least one live deployment input.

18 Claims, 10 Drawing Sheets

(56) References Cited

U.S. PATENT DOCUMENTS

| | | | |
|---|---|---|---|
| 2021/0045716 A1* | 2/2021 | Shiran | G06T 7/246 |
| 2021/0093300 A1* | 4/2021 | Nakahara | A61B 8/0891 |
| 2021/0100530 A1* | 4/2021 | Park | G16H 50/20 |

OTHER PUBLICATIONS

Mostafa Jahanifar, Neda Zamani Tajeddin, Meisam Hasani, Babak Shekarchi, Kamran Azema. 'Automatic Recognition of the Supraspinatus Tendinopathy from Ultrasound Images using Convolutional Neural Networks' arXiv:2011.11777; https://doi.org/10.48550/arXiv.2011.11777 (Year: 2020).*

Leitner, Christoph, et al. "Automatic tracking of the muscle tendon junction in healthy and impaired subjects using deep learning." 2020 42nd Annual International Conference of the IEEE Engineering in Medicine & Biology Society (EMBC). IEEE, 2020. (Year: 2020).*

Cronin, Neil J., Taija Finni, and Olivier Seynnes. "Fully automated analysis of muscle architecture from B-mode ultrasound images with deep learning." arXiv preprint arXiv:2009.04790 (2020). (Year: 2020).*

Blaivas, Michael et al. "Creation and Testing of a Deep Learning Algorithm to Automatically Identify and Label Vessels, Nerves, Tendons, [...]" Journal of ultrasound in medicine : official journal of the American Institute of Ultrasound in Medicine vol. 39,9 (2020): 1721-1727. doi: 10.1002/jum.15270 (Year: 2020).*

Cronin, N. (2020). Automated Analysis of Musculoskeletal Ultrasound Images Using Deep Learning. Cognitive Computing and Collective Intelligence, Master's Thesis. Faculty of Information Technology. University of Jyväskylä.

Jabbar, S. I., Day, C. R., Heinz, N., & Chadwick, E. K. (2016). Using Convolutional Neural Network for Edge Detection in Musculoskeletal Ultrasound Images. 2016 International Joint Conference on Neural Networks (IJCNN).

Boussouar, A., Meziane, F., & Crofts, G. (2017). Plantar fascia segmentation and thickness estimation in ultrasound images. Computerized Medical Imaging and Graphics 56 (2017) 60-73.

Kuok, C., Yang, T., Tsai, B., Jou, I., Horng, M., Su, F., & Sun, Y. (2020). Segmentation of finger tendon and synovial sheath in ultrasound image using deep convolutional neural network. BioMedical Engineering OnLine. 2020; 19-24. Retrieved from https://www.ncbi.nlm.nih.gov/pmc/articles/PMC7178953/.

Shin, Y., Yang, J., Lee, Y. H., & Kim, S. (2021). Artificial intelligence in musculoskeletal ultrasound imaging. Ultrasonography 2021; 40:30-44. Retrieved from https://doi.org/10.14366/usg.20080.

Benrabha, J., Meziane, F. (2017). Automatic ROI detection and classification of the achilles tendon ultrasound images. IML '17 Proceedings of the 1st International Conference on Internet of Things and Machine Learning. 2017; 69: 1-7. Retrieved from http://usir.salford.ac.uk/id/eprint/43745/.

\* cited by examiner

METHOD AND SYSTEM FOR IDENTIFYING A TENDON IN ULTRASOUND IMAGING DATA AND VERIFYING SUCH IDENTITY IN LIVE DEPLOYMENT

TECHNICAL FIELD

This disclosure relates to ultrasound imaging. In particular, it relates to systems and methods for training and deploying an artificial intelligence (AI) model to identify and measure musculoskeletal tissue, namely tendons.

BACKGROUND

Ultrasound is a useful, non-invasive imaging technique capable of producing real time images of internal structures within tissue. Ultrasound imaging has an advantage over X-ray imaging in that ultrasound imaging does not involve ionizing radiation. Some mobile ultrasound scanners, including app-based ultrasound scanners, communicate with an add-on device that can act as both as a display and a control device. Examples of these add-on devices are mobile phones, tablets, laptops or desktop computers.

Ultrasound has also been applied, more recently, for the dynamic imaging of small body structures and the evaluation of the ligaments, muscle tendons and peripheral nerves. Technology advances including refined transducer technology, power Doppler sonography, and real-time ultrasound elastography (EUS), have expanded its clinical applications in the field of musculoskeletal imaging. Coupled with this, innovations to enhance spatial resolution and image quality, such as speckle reduction, video capturing, harmonic tissue imaging, compound imaging, and panoramic imaging, are the direct product of developments in computing power and algorithms.

Applying ultrasound scanning to musculoskeletal structures is, however, not without challenges. While AI-based musculoskeletal ultrasound models have shown promise in overcoming high variability and operator dependency, there are limitations to be addressed. First, due to the complexity of musculoskeletal structures, image preprocessing techniques such as rigid or non-rigid image registration are required for the large-scale application of ultrasound deep learning. In addition, there are identification and diagnosis challenges based on 2D ultrasound, in the absence of a comprehensive understanding of functional anatomy. Second, artifacts within ultrasound images of musculoskeletal structures, may either be mistaken for pathology or artifacts can occur together with abnormal conditions in both gray-scale and Doppler imaging. As such, the careful acquisition of quality AI training data is paramount for musculoskeletal US imaging.

Third, an ultrasound user's adjustments and further optimization may lead to additional high variability and randomness, which limit the accuracy and reproducibility of AI models and in particular, for musculoskeletal US imaging. In regard to tendons, the quality of images may be affected and compromised by the presence of speckle noise/speckle artifacts which may diffuse the image edges, making medical interpretation and measurements challenging, and therefore impacting the accuracy of use, diagnosis and treatment options based upon such images. B-mode ultrasound images are characterized by these speckle artifacts, which introduce fine-false structures whose apparent resolution is beyond the imaging system capabilities. Speckle presence is due to interference effects between overlapping echoes and its occurrence is related to a great number of randomly distributed structure scatterers within a resolution cell.

For at least these reasons, optimization of AI-based musculoskeletal ultrasound applications will increase accuracy and adoption (particularly for non-experts), such optimization and improvements for enabling quick and accurate localization, identification and verification of the musculoskeletal feature or region of interest.

The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate one or more of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF DRAWINGS

The following drawings illustrate embodiments of the invention and should not be construed as restricting the scope of the invention in any way.

DETAILED DESCRIPTION

A. Glossary

Figure 1:
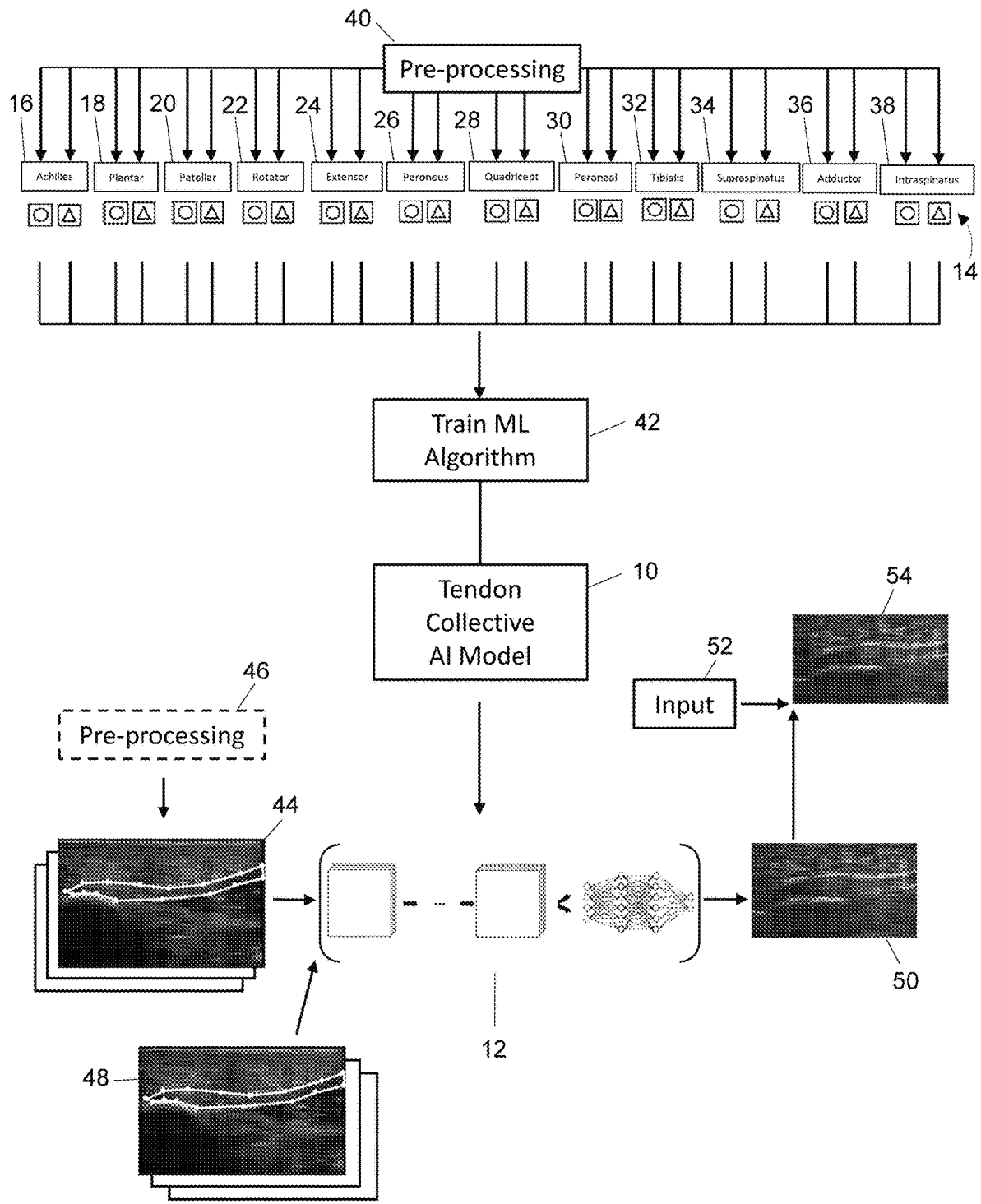
FIG. 1 is a schematic diagram of the training and deployment of an AI model, according to an embodiment of the present invention.

The term "AI model" means a mathematical or statistical model that may be generated through artificial intelligence techniques such as machine learning and/or deep learning. For example, these techniques may involve inputting labeled or classified data into a neural network (e.g., a deep neural network) algorithm for training, so as to generate a model that can make predictions or decisions on new data without being explicitly programmed to do so. Different software tools (e.g., TensorFlow™, PyTorch™, Keras™) may be used to perform machine learning processes.

The term "module" can refer to any component in this invention and to any or all of the features of the invention without limitation. A module may be a software, firmware or hardware module, and may be located, for example, in the ultrasound scanner, a display device or a server.

The term "communications network" can include both a mobile network and data network without limiting the term's meaning, and includes the use of wireless (e.g. 2G, 3G, 4G, 5G, WiFi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "operator" (or "user") may refer to the person that is operating an ultrasound scanner (e.g., a clinician, medical personnel, a sonographer, ultrasound student, ultrasonographer and/or ultrasound technician).

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to a system for identifying a tendon of interest and, in live deployment, corroborating such identity by at least one input in order to reduce false positive identifications, the system being a subject of the present invention. In various embodiments, the system may include an ultrasound machine (including a display and one or more transducers); an ultrasound scanner and a display device; and/or an ultrasound scanner, display device and a server.

The term "tendon" refers at least to the group consisting of: Patellar tendon, Plantar fascia, Achilles, Rotator cuff, Extensor, Peroneus, Quadricept, Peroneal, Tibialis, Adductor, Supraspinatus, and Intraspinatus, although this list is not intended to be limiting.

The term "ultrasound image frame" (or "image frame" or "ultrasound frame") refers to a frame of post-scan conversion data that is suitable for rendering an ultrasound image on a screen or other display device.

B. Exemplary Embodiments

At a high level, the embodiments herein generally allow for the provision of ultrasound systems and ultrasound-based methods for identifying and verifying musculoskeletal features/regions of interest, namely tendons, and medical conditions and anomalies therearound, such as for automatic measurement, and thereafter, diagnosis and treatment as and if required.

The embodiments herein further provide for the identification of a tendon in ultrasound imaging data, by deploying an artificial intelligence (AI) model to execute on a computing device, wherein the AI model is trained to identify a plurality of different types of tendons imaged in ultrasound imaging data, and when deployed, the computing device generates a probability for each of the plurality of different types of tendons that the type of tendon is imaged in new ultrasound imaging data. In addition, some of the embodiments provide for the AI model to process a new ultrasound imaging data to generate a degree of probability for each of the plurality of different types of tendons that the type of tendon is imaged in the new ultrasound imaging data while using an input to corroborate the generated degree of probability for a tendon type of the plurality of different types of tendons, thereby accurately matching a selected and corroborated tendon. The combination of the trained "tendon specific" AI model, enabled by the particularly hyperechoic and fibrillar structure of tendons and the live deployment input(s) for corroboration may make the system and method of the present invention highly accurate even for inexperienced ultrasound users.

In some embodiments, the ultrasound frames of a plurality of different types of tendons imaged in ultrasound imaging data may be processed against an artificial intelligence (AI) model on a per pixel basis, and the probability that a type of tendon of the plurality of different types of tendons is imaged in new ultrasound imaging data may be generated on a per pixel basis. When deployed, an output of the AI model for a first pixel of the new ultrasound imaging data may be used to corroborate the output of the AI model for a second pixel of the new ultrasound imaging data adjacent or within the proximity to the first pixel.

Alternatively, the ultrasound frames of a plurality of different types of tendons imaged in ultrasound imaging data may be processed against an artificial intelligence (AI) model on a line/sample basis, and the probability that a type of tendon of the plurality of different types of tendons may be imaged in new ultrasound imaging data is generated on a line/sample basis.

Within the scope of the present invention, an AI model is trained to identify a plurality of different types of tendons imaged in ultrasound imaging data, and when deployed, a processor with at least one computing device: i) generates a probability for each of the plurality of different types of tendons that the type of tendon is imaged in new ultrasound imaging data; ii) receives at least one input indicating a specific type of the plurality of different types of tendons desired to be scanned (the "selected tendon"); iii) generates a degree of probability for each of the plurality of different types of tendons that the type of tendon is imaged in the new ultrasound imaging data; iv) corroborates the generated degree of probability for a tendon type of the plurality of different types of tendons; and finally, v) determines that the tendon type of the plurality of different types of tendons is imaged in the new ultrasound imaging data (the "corroborated tendon type"). This identification and "live deployment" input-based corroboration is only possible by the provision of a suitably trained multi-tendon-based AI model.

Tendons are a soft connective tissue designed to efficiently transfer loads generated by muscles to the skeletal system, facilitating joint movement and can be found as rounded cords, strap-like bands, or flattened ribbons, depending on their function. As described further below, they exhibit a complex hierarchical structure arranged longitudinally to resist the direction of most tension. Disease of the tendon, known as tendinopathy, is characterized by pain and reduced mobility and functionality. The pathology is complex, including disordered healing causing fiber disruption and disorientation, generally with an absence of inflammatory cells. The etiology and progression of the disease are not well known, leading experts to coin the term 'tendinopathy' to describe the clinical presentation of the condition. The prevalence of tendinopathy has been estimated at 11.83 per 1000 persons per year, with an incidence rate of 10.52 per 1000 persons per year and Achilles tendinopathy has been reported to be as prevalent as 6-9% of some populations with 4% of sufferers going on to suffer rupture of the tendon. As such, the easy acquisition of accurate ultrasound images of both healthy and injured tendons is critically important, including in medical settings without access to trained radiologists. Improved ultrasound technologies in this space is expected to be favourably received.

It has been found that tendons, as compared to many other anatomical features, are uniquely suited to the method and system of the present invention due to their particularly uniform (yet complex) structure, even across varying types of tendons. This structure of tendons makes them uniquely suited to their role connecting muscle to bone throughout the body. They have a very high collagen content, mostly Type I collagen, arranged in a cross-linked triple-helix structure. Tightly bound water molecules bridge the strands of the helix, stabilizing the structure and allowing hydrogen bonding to further water molecules, all of which are confined to the transverse plane of the tendon. There is a complex, hierarchical structure with collagen macromolecules grouped into fibrils, which, in turn, are bundled into fibers and fascicles surrounded by vascularized connective tissue endotendon, which are in turn bound together to form the tendon. A tendon sheath, comprising two layers of synovium, is typically seen surrounding tendons that pass through tight fibro-osseous tunnels or around corners, such as those at the wrist and ankle.

Regarding ultrasound imaging, tendons exhibit a hyperechoic fibrillar structure. Hyperechoic tissues generate a greater echo usually displaying as lighter colors during ultrasound imaging. In a longitudinal plane, tendons have a fibrillar pattern with parallel hyperechoic lines (collagen fibers) in a structure evidencing intermediate echogenicity (matrix proteoglycan). In a transverse plane, tendons have a hyperechoic round to ovoid appearance and contain bright stippled clustered dots. Tears and damage within tendon exhibit as anechoic (appearing black with no internal echoes) or hypoechoic (less echogenic or darker than normal) defects.

Building a tendon specific AI model and using such a model with live deployment input(s) for corroboration of selected tendon identity has not previously been undertaken or the benefits thereof appreciated. Further details, embodiments, and features are described herein.

Referring to FIG. 1, shown there generally is a schematic diagram of a training and deployment of an AI model 10. According to an embodiment of the present invention, there is shown a method of training a neural network 12 to identify a plurality of tendon types, wherein each type depicted by a plurality of ultrasound images. Specifically, during use and deployment, neural network 12 creates a degree of probability for each the plurality of different types of tendons that the type of tendon is imaged in any new ultrasound imaging data. Subsequently, corroboration is provided via at least one input.

Training ultrasound frames are indicated generally across level 14, with each sample image depicting one or more sample frames of a plurality of tendons (for example and illustration): Achilles sample frames (16); Plantar fascia sample frames (18); Patellar sample frames (20); Rotator sample frames (22); Extensor sample frames (24); Peroneus sample frames (26); Quadricept sample frames (28); Peroneal sample frames (30); Tibialis sample frames (32); Supraspinatus sample frames (34); Adductor sample frames (36) and Intraspinatus sample frames (38). The training ultrasound frames (16-38) may include ultrasound frames A (denoted for each frame in FIG. 1 by circle in a box) with features that are tagged as acceptable and representative of each specific tendon, and/or ultrasound frames U (denoted for each frame in FIG. 1 by triangle in a box) that are tagged respectively as unacceptable and unrepresentative of each specific tendon.

For example, anatomical features on a given training ultrasound frame may be labeled A as acceptable of a given tendon if the fascicular structure is seen as multiple, closely spaced hyperechoic parallel lines on longitudinal scanning and if in the transverse plane multiple hyperechoic dots or lines are visible. While nearby ligaments also appear as hyperechoic structures, they tend to be less hyperechoic than tendons, in keeping with their less regular structure. With regard to nearby muscles, tendons may share a similar fibrillar appearance however given that they are denser, they will appear more hyperechoic relatively and such can be distinguished in the training ultrasound frames. In contrast, features on a given training ultrasound frame may be labeled U as unacceptable if they exhibit less dense, less fibrillary qualities which are indicative of other non-tendonous but (most likely) tendon-adjacent anatomy. With regards to differentials between a plurality of tendons, a given training ultrasound frame may be labeled A as an acceptable representation of a particular selected tendon (by a trainer/user) and labeled U as an unacceptable representation of a particular selected tendon (by a trainer/user). Both the training ultrasound frames labeled as A and U, for each particular type of tendon, may themselves be used for training and/or reinforcing AI model 10. This is shown in FIG. 1 with tracking lines from both A and U, for every set of training ultrasound frames 16-38, to training algorithm step 42.

In some embodiments, an optional pre-processing act 40 may be performed on the underlying ultrasound image frames 16-38 to facilitate improved performance and/or accuracy when training the machine learning (ML) algorithm. For example, it may be possible to pre-process the ultrasound images 16-38 through a high contrast filter to reduce the granularity of greyscale on the ultrasound images 16-38.

Additionally, or alternatively, it may be possible to reduce scale of the ultrasound images 16-38 prior to providing the ultrasound images 16-38 to the training algorithm step 42. Reducing the scale of ultrasound images 16-38 as a preprocessing step may reduce the amount of image data to be processed during the training act 42, and thus may reduce the corresponding computing resources required for the training act 42 and/or improve the speed of the training act 42.

Various additional or alternative pre-processing acts may be performed in act 40. For example, these acts may include data normalization to ensure that the various ultrasound frames 16-38 used for training have generally the same dimensions and parameters.

Referring still to FIG. 1, the various training frames 16-38 may, at act 42, be used to train a ML algorithm. For example, the various training ultrasound frames 16-38, may be inputted into deep neural network 12 that can learn how to predict identity probabilities of new ultrasound images as compared to all trained and stored tendon images. For example, the neural network may learn to detect tendons and to discard the presence of differing nearby anatomical features such as ligaments and muscles around a given tendon.

The result of the training may be the AI model 10, which represents the mathematical values, weights and/or parameters learned by the deep neural network to identity probabilities for new ultrasound images as compared to all trained and stored tendon images. The training act 42 may involve various additional acts (not shown) to generate a suitable AI model 10. For example, these various deep learning techniques such as regression, classification, feature extraction, and the like. Any generated AI models may be iteratively tested to ensure they are not overfitted and sufficiently generalized for creating the comparison and list of probabilities in accordance with method of the invention.

In some embodiments, using a cross-validation method on the training process would optimize neural network hyper-parameters to try to ensure that the neural network can sufficiently learn the distribution of all possible tendon image types without overfitting to the training data. In some embodiments, after finalizing the neural network architecture, the neural network may be trained on all of the data available in the training image files.

In various embodiments, batch training may be used and each batch may consist of multiple images, thirty-two for example, wherein each example image may be gray-scale, preferably 128*128 pixels although 256*256 pixels and other scaled may be used, without any preprocessing applied to it.

In some embodiments, the deep neural network parameters may be optimized using the Adam optimizer with hyper-parameters as suggested by Kingma, D. P., Ba, J. L.: Adam: a Method for Stochastic Optimization, International Conference on Learning Representations 2015 pp. 1-15 (2015), the entire contents of which are incorporated herewith. The weight of the convolutional layers may be initialized randomly from a zero-mean Gaussian distribution. In some embodiments, the Keras™ deep learning library with TensorFlow™ backend may be used to train and test the models.

In some embodiments, during training, many steps may be taken to stabilize learning and prevent the model from over-fitting. Using the regularization method, e.g., adding a penalty term to the loss function, has made it possible to prevent the coefficients or weights from getting too large. Another method to tackle the over-fitting problem is dropout. Dropout layers limit the co-adaptation of the feature extracting blocks by removing some random units from the neurons in the previous layer of the neural network based on the probability parameter of the dropout layer. Moreover, this approach forces the neurons to follow overall behaviour. This implies that removing the units would result in a change in the neural network architecture in each training step. In other words, a dropout layer performs similar to adding random noise to hidden layers of the model. A dropout layer with the dropout probability of 0.5 may be used after the pooling layers.

Data augmentation is another approach to prevent overfitting and add more transitional invariance to the model. Therefore, in some embodiments, the training images may be augmented on-the-fly while training. In every mini-batch, each sample may be translated horizontally and vertically, rotated and/or zoomed, for example. The present invention is not intended to be limited to any one particular form of data augmentation, in training the AI model. As such, any mode of data augmentation which enhances the size and quality of the data set, and applies random transformations which do not change the appropriateness of the label assignments may be employed, including but not limited to image flipping, rotation, translations, zooming, skewing, and elastic deformations.

Referring still to FIG. 1, after training has been completed, the sets of parameters stored in the storage memory may represent a trained neural network of a plurality of tendon types to predict identity probabilities of new ultrasound images as compared to each trained and stored tendon image type.

In order to assess the performance of AI model 10, the stored model parameter values can be retrieved any time to perform image assessment through applying an image to the neural networks (shown as 12) represented thereby.

In some embodiments, the deep neural network may include various layers such as convolutional layers, pooling layers, and fully connected layers. In some embodiments, the final layers may include a softmax layer as an output layer having outputs which eventually would demonstrate respective determinations that an input set of pixels fall within a particular area above or below a tendon boundary, in the training images. Accordingly, in some embodiments, the neural network may take at least one image as an input and output a binary mask indicating which pixels belong to the area above the tendon boundary (e.g., the AI model classifies which area each pixel belongs to).

To increase the robustness of the AI model 10, in some embodiments, a broad set of training data may be used at act 42. For example, it is desired that ultrasound images of a plurality of tendon types, both transverse and longitudinally, and at differing frequencies, depths and gains be included in the training ultrasound images 16-38.

More specifically, training medical images 16-38 may be labeled with one or more features associated with/are hallmarks of a selected tendon (e.g.; Achilles tendon presenting a different size and orientation that Plantar fascia tendon). This may include identifying a variety of features visualized in the captured training medical image. In at least some embodiments, this data may be received from trainer/user input. For example, a trainer/user may label the features relevant for the application visualized in each training image.

The image labelling can be performed, for example, by a trainer/user observing the training ultrasound images, via a display screen of a computing device, and manually annotating the image via a user interface. In some aspects, the training ultrasound images used for the method herein will only be images in which the image quality is of a sufficient quality threshold to allow for proper and accurate feature identification. For example, this can include training ultrasound images having a quality ranging from a minimum quality in which target features are just barely visible for labelling (e.g., annotating), to excellent quality images in which the target features are easily identifiable. In various embodiments, the training medical images can have different degrees of images brightness, speckle measurement and SNR. Accordingly, training ultrasound images 16-38 can include a graduation of training medical images ranging from images with just sufficient image quality to high image quality. In this manner, the machine learning model may be trained to identify features on training medical images that have varying levels of sufficient image quality for later interpretation and probability assessment.

Due to issues around the anisotropy in the ultrasound imaging of tendons, they are best imaged using a linear transducer aligned perpendicular to the axis of the collagen fibers, whenever possible. However, unskilled or novice ultrasound operators may not have developed the skillset to obtain the correct viewing angles, particularly for a variety of different tendon types. Thus, training AI model 10, with off-angle ultrasound images may increase the robustness of the model, so as to be operational and accurate when new tendon images are acquired by unskilled or novice operators. This is compounded by the fact that AI model 12 is trained on a plurality of tendon types, with differing curvatures, in varying locations in the body.

Figure 9:
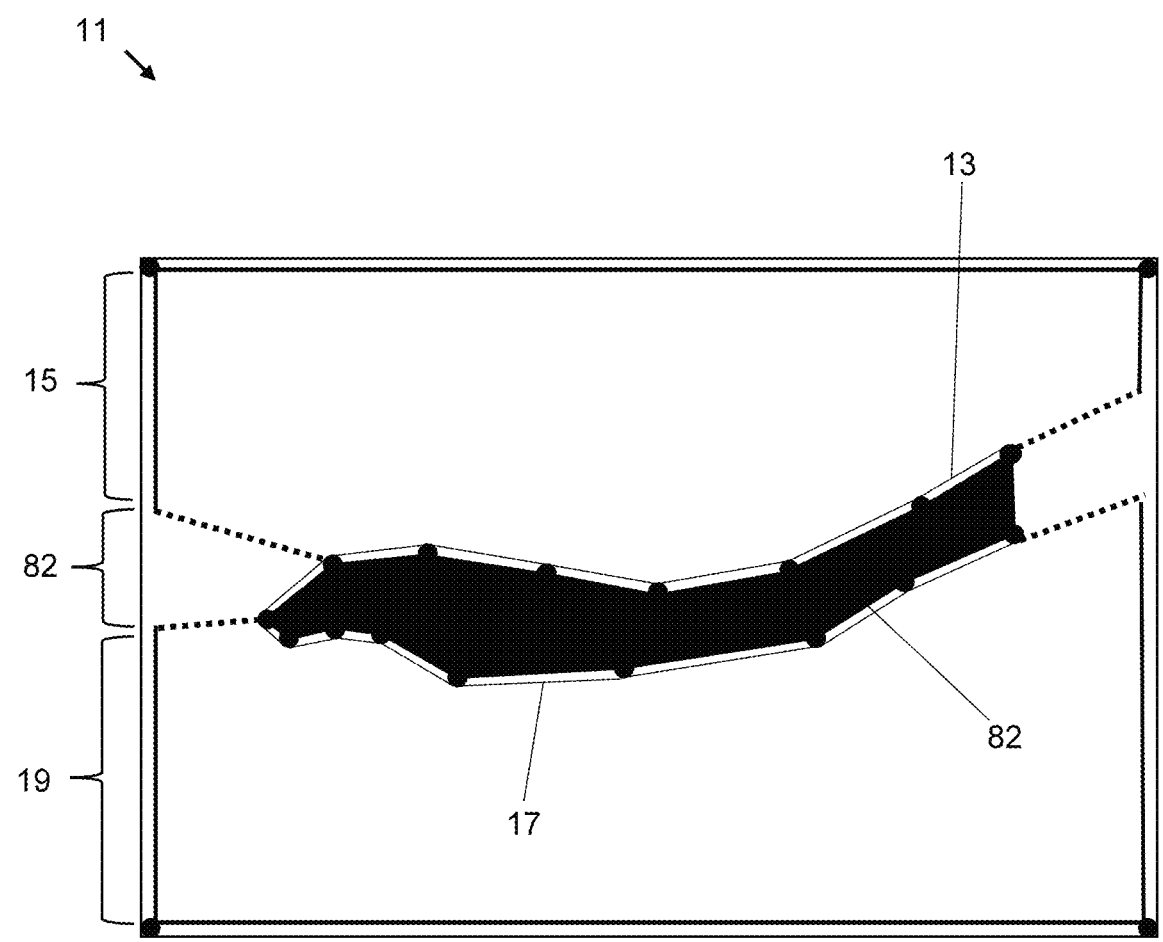
FIG. 9 is a schematic diagram of a tendon image showing two tendon boundaries for identifying, labeling and training an AI model, according to an embodiment of the present invention.

Overall, the scope of the invention and accorded claims are not intended to be limited to any one particular process of training AI model 10. Such examples are provided herein by way of example only. AI model 10 may be trained by both supervised and unsupervised learning approaches at 42 although due to scalability, unsupervised learning approaches, which are well known in the art, are preferred. Other approaches may be employed to strengthen AI model 10. For example, referring to FIG. 9, image 11 of the tendon 82 may acquired rotationally off angle from the preferred angle which is aligned perpendicular to the axis of the collagen fibers within the tendon. An example tendon boundary 13 is shown that delineates between fibers and features of tendon 82 below first tendon boundary 13 and non-tendon anatomy above first tendon boundary 13. The images areas that are on the distal side 15 of first tendon boundary 13, relative to tendon 82 may be removed prior to labeling such images as acceptable (A) for training AI model 12. Similarly, second tendon boundary 17 may be provided on training ultrasound mages which are on a proximal side of tendon 82 and likewise images areas that are on the proximal side 19 may be removed prior to labeling such images as acceptable (A) for training AI model 10.

Referring again to FIG. 1, once a satisfactory AI model 10 is generated, the AI model 10 may be deployed for execution on a neural network 12 to generate a series of identity probabilities for new tendon ultrasound images 44. Notably, the neural network 12 is shown in FIG. 1 for illustration as a convolution neural network—with various nodes in the input layer, hidden layers, and output layers. However, in various embodiments, different arrangements of the neural network 12 may be possible.

In various embodiments, prior to being processed for assessment of identity probability, the new ultrasound images 44 may optionally be pre-processed. This is shown in FIG. 1 with the pre-processing act 46 in dotted outline. In some embodiments, these pre-processing acts 46 may be analogous to the pre-processing acts 40 performed on the training ultrasound frames 16-38 (e.g., processing through a high contrast filter and/or scaling), to better align the new ultrasound images 44 with the training tendon images 16-38, and thereby facilitate improved accuracy in predicting identity probabilities. For example, pre-processing an input image may help standardize the input image so that it matches the format (e.g., having generally the same dimensions and parameters) of the training ultrasound images 16-38 that the AI machine model 10 is trained on.

In various embodiments, the new ultrasound images 44 may be live images acquired by an ultrasound imaging system (e.g., the system discussed with respect to FIG. 8 below). For example, the AI model 10 may be deployed for execution on the scanner 131 and/or the display device 150 discussed in more detail below. Additionally, or alternatively, the AI model 10 may be executed on stored (as opposed to new) ultrasound images 48 that were previously acquired (e.g., as may be stored on a Picturing Archiving and Communication System (PACS)).

Whether the images are stored ultrasound images 48 or new ultrasound images 44, the AI model 10 enables the neural network 12 to generate probability for each of the plurality of different types of trained tendons that the type of tendon is imaged in the new/stored ultrasound imaging data, and create a probability-scale thereof, depicted as probability image 50.

Probability is a number that can be assigned to outcomes and events which is always greater than or equal to zero, and less than or equal to one. This can be written as $0 \leq P(A) \leq 1$. In other words, the sum of the probabilities of all outcomes must equal 1. Within the scope of the present invention, the AI model 10 enables the neural network 12 to generate a number from 0 to 1, with reference to at least one (and in some cases, more than one) of the tendons of trained ultrasound images 16-38, thereby assigning a probability that each tendon is present in new ultrasound image(s) 44 or the stored ultrasound image(s) 48. For example, a user may derive significant confidence that new ultrasound image(s) 44 or the stored ultrasound image(s) 48 is an Achilles tendon should the AI model generate 0.9 probability. In other instances, the level of probability may not be as clear. Hence, the additional corroboration provided within the scope of the invention may be desirable.

Probability image 50 may be further processed with data from input 52 which indicates a specific type of the plurality of different types of tendons desired to be scanned (the "selected tendon"). In one embodiment, input 52 comprises user selection, on an interface, of a selected tendon desired to be scanned. For example, user selection may be conveyed to a processor at a computing device (shown in FIG. 7) by at least one of voice command, ultrasound probe gesture or ultrasound input control coupled to a probe. In another embodiment, input 52 comprises data from a cloud-based storage conveyed to a processor at a computing device. When executed in this manner, a processor may use the input 52 to corroborate the generated degree of probability for a tendon type of the plurality of different types of tendons and based on such corroboration, may determine that the tendon type of the plurality of different types of tendons is imaged in the new ultrasound image(s) 44/stored ultrasound image (s) 48, thereby creating a corroborated tendon type image 54, which may then be used for the generation of a 2D or 3D representation of the selected tendon.

Figure 2:
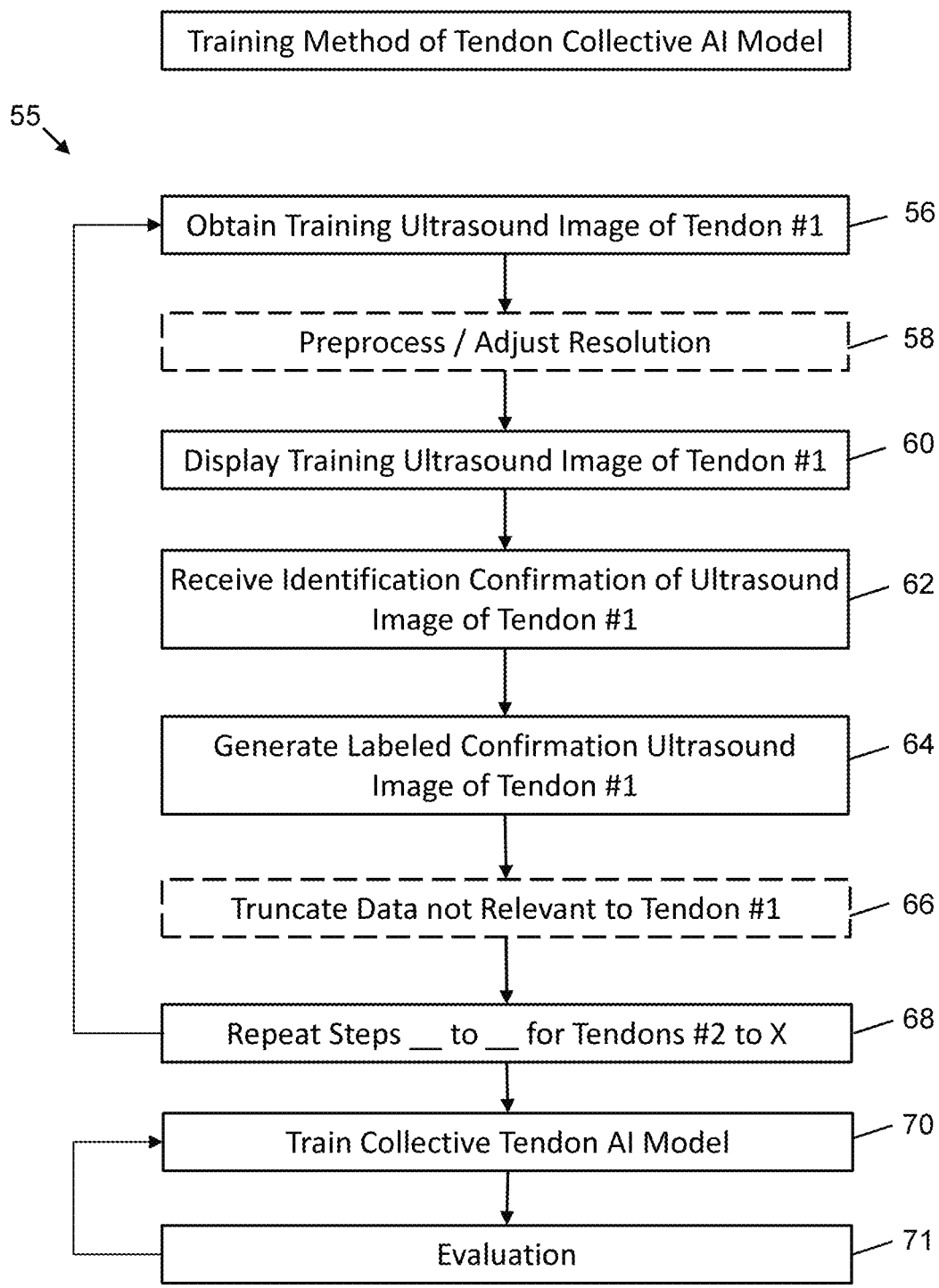
FIG. 2 is flowchart diagram of the steps for training the AI model, according to an embodiment of the present invention.

FIG. 2 is flowchart diagram of the steps for training the AI model of FIG. 1, according to an embodiment of the present invention. Method 55 is described below with regard to the systems and components depicted in FIG. 7, though it should be appreciated that method 55 may be implemented with other systems and components without departing from the scope of the present disclosure. In some embodiments, method 55 may be implemented as executable instructions in any appropriate combination of the imaging system 130, for example, an external computing device connected to the imaging system 130, in communication with the imaging system 130, and so on. As one example, method 55 may be implemented in non-transitory memory of a computing device, such as the controller (e.g., processor) of the imaging system 130 in FIG. 7. At 56, method 55 may include acquiring a dataset of sample images for training the neural network. Each sample image in the dataset may be a sample ultrasound image depicting a sample tendon.

Figure 7:
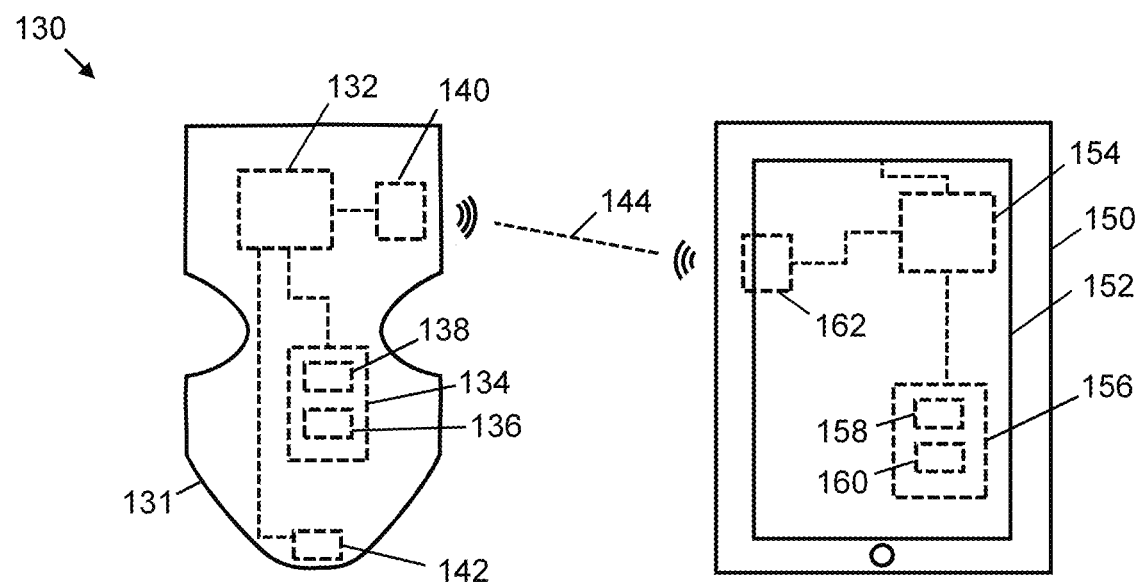
FIG. 7 is a schematic diagram of an ultrasound imaging system, according to an embodiment of the present invention.

Referring still to FIG. 2, in step 56, a training ultrasound image may be obtained. For example, a training ultrasound image may be acquired by the scanner 131 (as shown in FIG. 7) transmitting and receiving ultrasound energy. The training ultrasound image may generally be a post-scan converted ultrasound image. While the method of FIG. 2 is described in relation to a single training ultrasound image, the method may also apply to the use of multiple training ultrasound images. While the method of FIG. 2 is described in relation to a post-scan ultrasound image, it is to be understood that pre-scan images, may be used, as described in U.S. patent application Ser. No. 17/187,851 filed Feb. 28, 2021, the entire contents of which are incorporated herein by reference.

Optionally, in step 58 (as shown in dotted outline), the resolution of the training ultrasound image may be adjusted. For example, the resolution may be increased or decreased. The purpose of this may be to provide the labeler (e.g., a medical professional with relevant clinical expertise) with training ultrasound images that have a more standardized appearance. This may help to maintain a higher consistency with which the labeler identifies anatomical features in the training ultrasound images. Besides the resolution, other parameters of the training ultrasound image may also be adjusted such as input scaling, screen size, pixel size, aspect ratio, and the removal of dead space, as described above (including, for example, data augmentation and other pre-processing steps).

In step 60, the training ultrasound image may be displayed on a display device, such as the display device 150 discussed in more detail below in relation to FIG. 7. The labeler can then identify a particular tendon in the training ultrasound image by, for example, tagging it with a name from a pull-down menu (e.g., as described below in relation to FIG. 3). The labeler then can mark the training ultrasound image around the particular tendon that the labeler has identified in the training ultrasound image. Again, the labeler may use techniques such as those described below in relation to FIG. 3. In step 62, the system that is used for the training may receive the identification of the tendon. In step 64, the system may generate, from the labeler's marking inputs, a labeled training ultrasound image, and display it on the display device. In various embodiments, steps 62 and 64 may readily be interchanged with each other.

Once the training ultrasound image has been marked and labeled, the system may then remove, in step 66, optionally, (as shown in dotted outline), regions of the labeled ultrasound data frame that are both outside the area of the identified tendon and outside areas relevant for the AI model to recognize the particular tendon. For example, the labeled ultrasound data frame may be truncated at one or more sides. Additionally, or alternatively, the data at deeper depths on labeled ultrasound data frame may be truncated if the tendon is at a relatively shallower portion of the labeled ultrasound data frame. Truncation of some of the ultrasound data may allow the training of the AI model to proceed more quickly. At step 68, there is provided a redirection to complete steps 56-68 a plurality of times, both for a first tendon and subsequent tendons thereby to build a robust tendon-specific AI model. At step 70, the labeled raw ultrasound data frame is then used for training the AI model 10. At step 71, once training is completed, the AI model may be used to perform predictions on an unseen dataset to validate its performance such evaluation at step 71 feeding data back to train the AI model at step 70.

Figure 3:
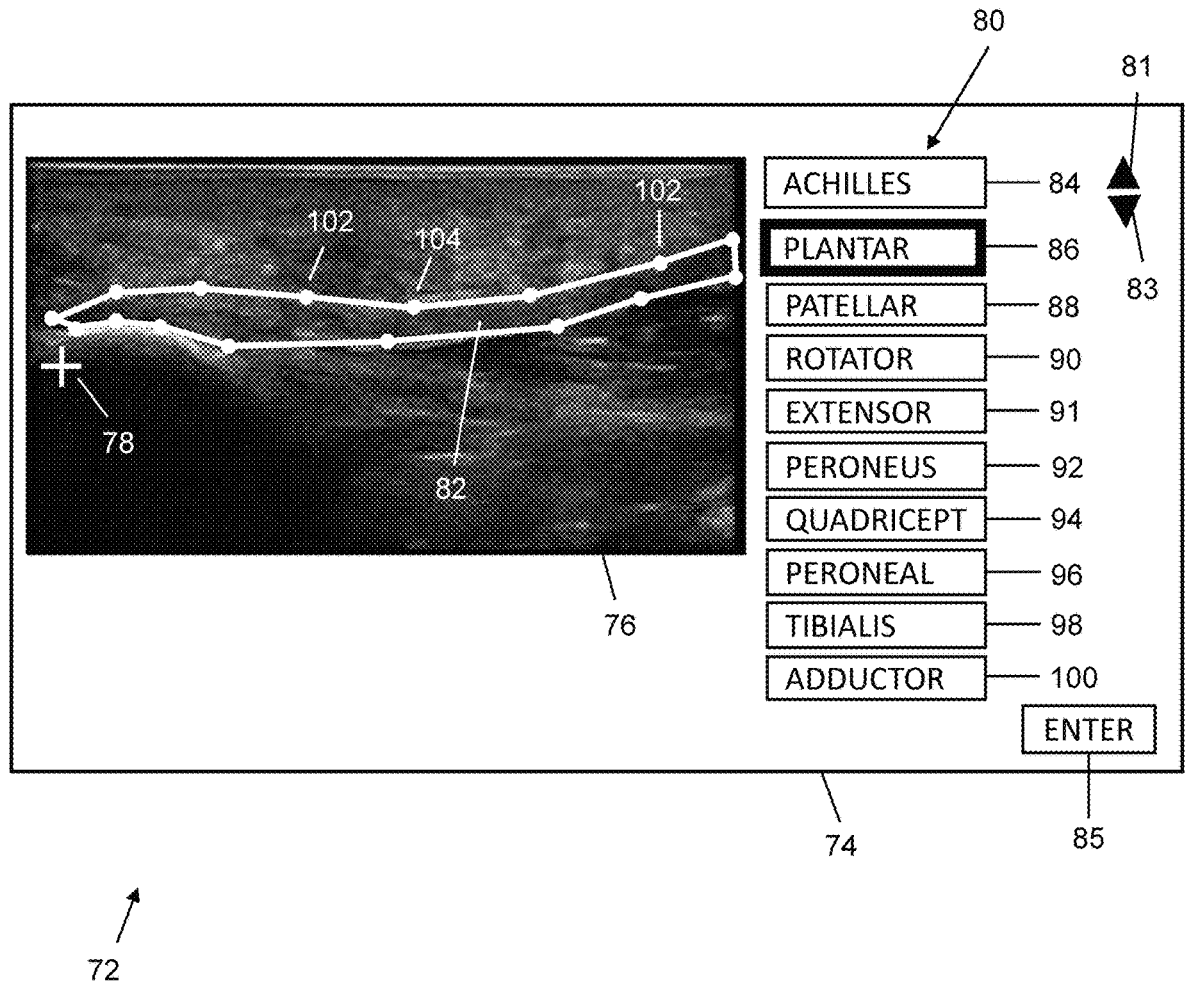
FIG. 3 is a schematic diagram of a user interface for training the AI model, displaying a scanned region of interest (in this case appearing to be a segmented ultrasound image of a plantar fascia tendon), along with user input options relating to specific tendons, according to an embodiment of the present invention.

Referring to FIG. 3, there is provided a schematic diagram of a user interface (generally indicated at 72) for training AI model 10. An example user interface screen 74 is shown for labeling a training ultrasound image 76. The user interface screen 74 may be displayed on a computer, such as a laptop computer, a desktop computer or a tablet. In the example shown, the user interface screen 74 includes a cursor 78, which the user (e.g., ultrasound labeler, or labeler) may move around over the training ultrasound image 76 and, at various points on the image, use it to mark the image. For example, the user may use the cursor 78 to mark individual points around a particular tendon present in the training ultrasound image 76, and/or to draw an enclosing line around a particular tendon. Also present in the user interface screen 74 is a pull-down menu generally shown as 80 (with directional arrows 81 and 83 and "Enter" button 85), which may list various tendons that the user may identify in the training ultrasound image 76. In use, the user may mark a tendon 82 (as shown, Plantar fascia) with the cursor 78 and label the marked tendon with a corresponding choice from the pull-down menu 80, to result in a labeled training ultrasound image. Pull-down menu may open to a variety of selections, each denoting a different tendon, here shown by way of example 84 to 100 as follows: Achilles 84, Plantar 86, Patellar 88, Rotator 90, Extensor 91, Peroneus 92, Quadricept 94, Peroneal 96, Tibialis 98, and Adductor 100.

Referring still to FIG. 3, displayed over the training ultrasound image 76 and around the tendon are points 102 that have been created by the user clicking when the cursor 78 was located at those points 102. The points 102 are connected by lines 104 that are generated and displayed by the user interface 74. The lines 104 trace around the tendon, which has been labeled by the user by selecting a named specific tendon (one of, for example, 84-100) given by the pull-down menu 80. In this example, the tendon identified by the user is a plantar fascia, which is shown by emboldening the selected menu option 86. After the tendon has been marked and labeled, an 'Enter' button 85 is displayed on the user interface 74. The 'Enter' button 85 may be clicked, or otherwise activated, to submit the labeled training ultrasound image 76, with label 86, to the system for training the AI model.

In some embodiments, the user interface 76 may use other techniques for marking the tendon(s) during training of AI model 10. For example, circles, ovals, squares, rectangles, and other shapes of mask may be used, or shading or highlighting may be used. The main requirement is that the technique identify the area in the training ultrasound image 76 that represents the tendon of interest. The identified area may be expressed, for example, as a range of individual pixels, a regular polygon defined by the pixels at its vertices, an irregular polygon defined by the pixels at its vertices, an enclosed curve that is spline fitted to pixels marked by a user, and/or a freeform shape defined by a combination of fitted curves and straight lines to pixels identified by the user. In some cases, one, some or all of the pixels may be calculated by the system based on smoothing the inputs from the user.

It is not necessary for the user to exactly outline the tendon, as the AI model may compensate for any dither in the marking that the user makes. In some embodiments, the user has the option of editing the individual points 102 or the shape marked on the training ultrasound image 76.

Figure 4:
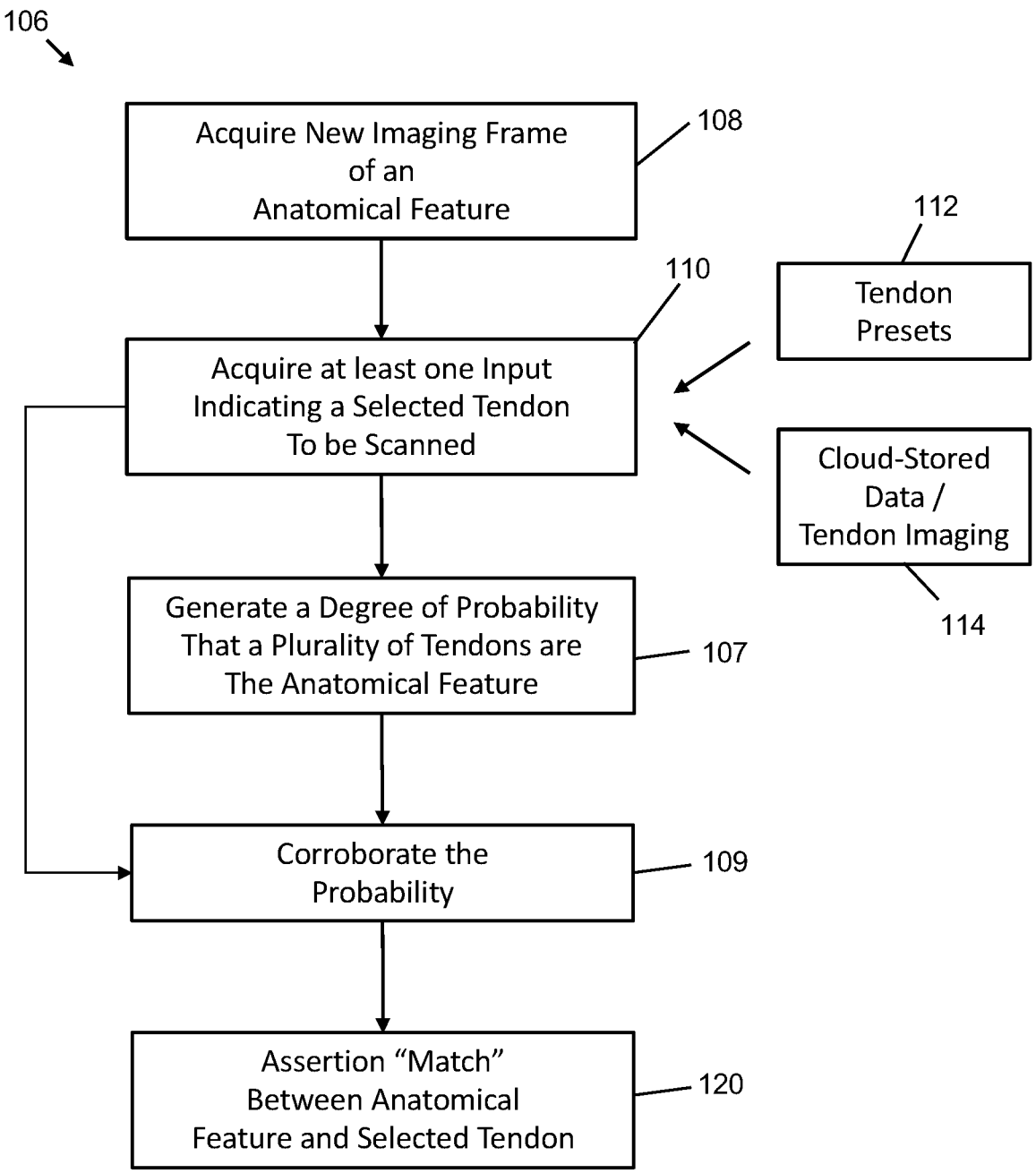
FIG. 4 is a flowchart diagram of an example method of image acquisition, identification and verification according to an embodiment of the present invention.

Referring to FIG. 4, a flowchart diagram of a method, generally indicated at 106, of new image acquisition, identification and corroboration according to at least one embodiment of the present invention is shown. Method 106 further supports and aligns with elements 10, 12, 44, 46, 48, 50 52 and 54 described above in FIG. 1. At 108, the ultrasound imaging system (referred to in FIG. 7), may acquire ultrasound imaging data. For example, a medical professional may operate an ultrasound scanner (hereinafter "scanner", "probe", or "transducer" for brevity) to capture images of a patient (whether human or animal). The ultrasound frames may be acquired by acquiring a series of a images (with a frame each containing a sequence of transmitted and received ultrasound signals) of different views of a tendon.

Although the Figures as provided herein illustrate post-scan converted ultrasound data, it should be appreciated that the medical imaging data may include raw or unprocessed data that cannot be directly displayed as an image. For example, in the case of ultrasound imaging data, the medical imaging data may include radio frequency (RF) data, pre-scan converted data, and/or post-scan converted data.

Further, at step 108, new ultrasound imaging data may be pre-processed and/or augmented as described above. At 110, input or inputs are collected which will serve, after step 116, to corroborate tendon identity at step 118. Such input comprises an indication of a specific type of the plurality of different types of tendons desired to be scanned, e.g., inputs indicating or suggesting the tendon desired to be scanned (referred to herein as "selected tendon"). Such input(s) may be collected during live deployment of method 106 and may be from a number of sources/origins including user tendon preset or workflow selection(s) on a live interface (112) and/or any tendon image data conveyed from a cloud-based storage (114) (e.g., previous exams stored on the cloud-based storage that may have indicated that a particular type of tendon was commonly being scanned by the medical practitioner). Whatever the input origin, the purpose is to aid in in situ corroboration of the AI model probability findings.

At step 116, AI model 10 generates a probability for each of the plurality of different types of tendons (trained within the AI model 10) that the type of tendon is imaged in the new ultrasound imaging data. For each tendon within the training model, a probability is assigned from 0 to 1. For example, a neural network may use the AI model to apply mathematical weights to different aspects of the tendon in the new image and creates a probability, for each pixel within the image, relating the new ultrasound imaging data to one or more tendon images trained within AI model. Such probability, valued from 0 to 1, enables the AI to select at least one tendon which most accurately matches the tendon in the new ultrasound imaging data.

Figure 10:
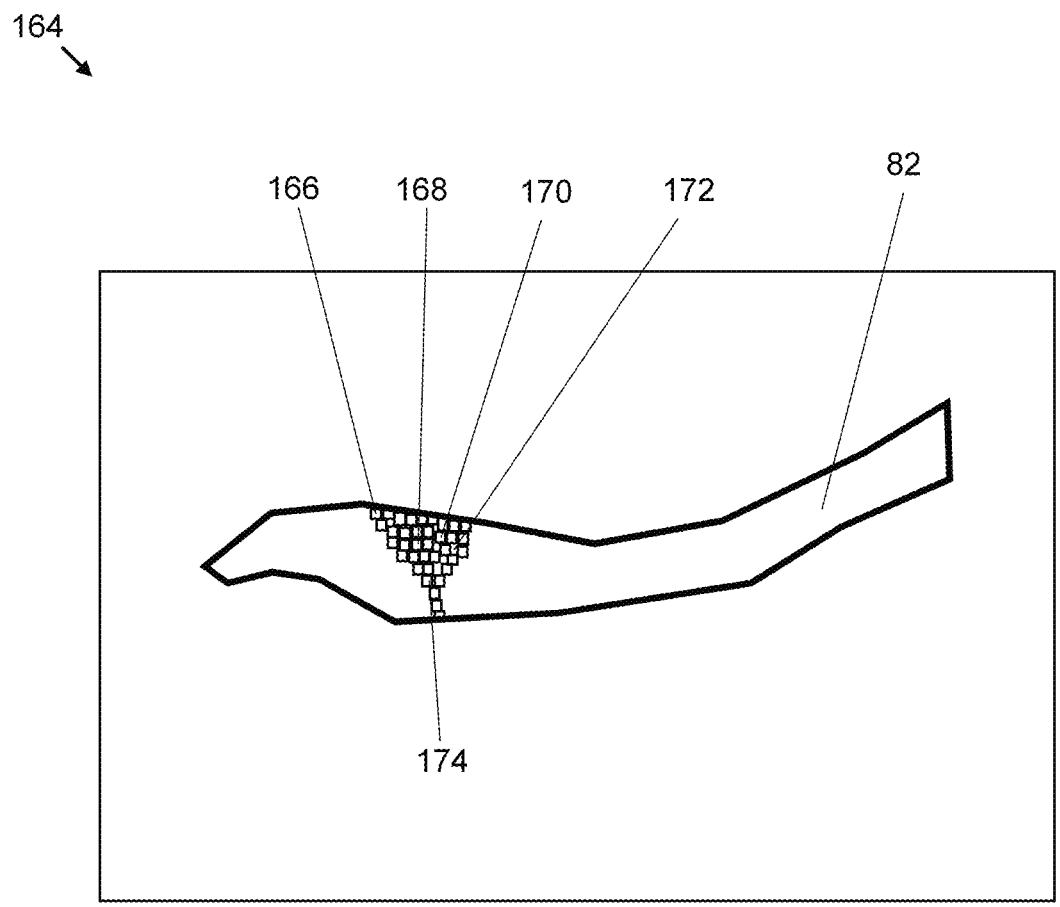
FIG. 10 is a schematic diagram of a tendon image showing assignment of pixel valuation for probability assessment by AI model, according to an embodiment of the present invention.

Referring to FIG. 10, which will assist in this aspect of the invention, there is a visual representation of such valuation and probability assignment, within image 164 of tendon 82. Tendon 82 is pixelated and, for illustration purposes, only five such pixels are identified: 166, 168, 170, 172 and 174. AI model 10 is employed by neural network 12 to identify features and aspects of the entirety of image 164 to create a probability, for each pixel within tendon 82, valued from 0 to 1 that, for each of the plurality of trained different types of tendons that tendon 82 is the "selected tendon". For example, pixels 166, 168, 170 and 172 may each be assigned or with, by the AI model 10, a 0.8 probability "score" of a match to a Plantar fascia tendon. Pixel 174 may be assigned 0.2 probability score of a match to an Achilles tendon. These probability values, for each and every pixel and with regard to every matched tendon are generated by the neural network 12 that employs AI model 10.

As shown in FIG. 10, the degrees of probability determined in act 116 may be provided on a per pixel basis. This means that for an area on the ultrasound image that corresponds to a tendon, it is possible that some pixels may be predicted to be one type of tendon while other pixels are predicted to be another type of tendon. In an example embodiment, a probability threshold (e.g., 0.75) can be used, and for pixels that have a probability score above the threshold, the most commonly predicted type of tendon can be outputted as the predicted tendon for the area on the image corresponding to the tendon. For example, for pixels that have an outputted probability score of 0.75 or higher, the majority of such pixels may predict that the tendon is plantar fascia while some others may predict the patellar tendon or the Achilles tendon. In this example, the predicted tendon may then be plantar fascia. However, in some embodiments, there may not be a clear majority for a predicted type of tendon. As such, it may be helpful to have an additional source of data to corroborate the output of the AI.

Turning back to FIG. 4, at step 118, the probability of identification (in step 116) is then corroborated by processing the at least one input, which at step 120 verifies if there is a match between the various types of tendon/anatomical features predicted for various pixels in the new ultrasound imaging data and the selected tendon. Since the output of the AI using AI model 10 may potentially predict different tendon types for different pixels, the input may be used as a source of information for what the operator is actually scanning, and thus this input can isolate a particular predicted tendon if there are multiple predicted types of tendons for various pixels.

the at least one input may be a user selection of a preset for the selected tendon, which may be conveyed to a computing device by at least one of voice command, ultrasound probe gesture or ultrasound input control coupled to a probe. Alternatively, the at least one input may be the receipt of cloud stored data for corroborating the generated degree of probability for the tendon type of the plurality of different types of tendons. Regardless of the specific type of input, it serves as a live deployment corroboration which significantly increases the accuracy of scan identifications for novice, training or less experiences users.

The present invention further provides for the automatic measurement and damage assessment (if any) of the selected and corroborated tendon. Tendinopathy has been associated with tendon enlargement and moreover, a thickening of a tendon is highly correlated with patient pain, so quantifying changes in tendon thickness may provide an indirect means of measuring function and monitoring treatments designed to reduce tendon hypertrophy. Actuating the measurement and/or degree of tendon damage without additional inputs from a user/operator is highly advantageous.

Figure 5:
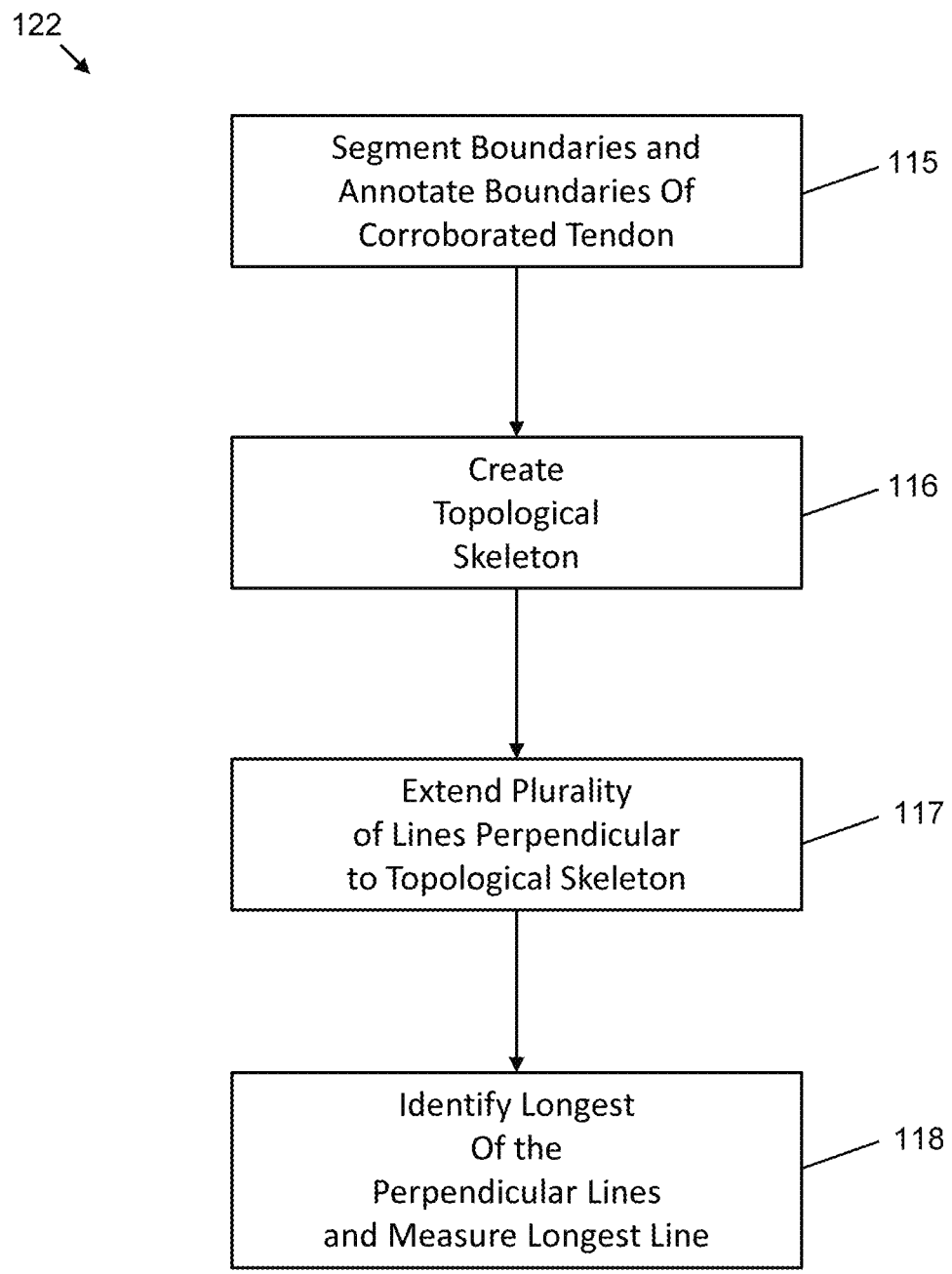
FIG. 5 is a flowchart for calculating the dimension of a selected tendon, according to an embodiment of the present invention.
Figure 11:
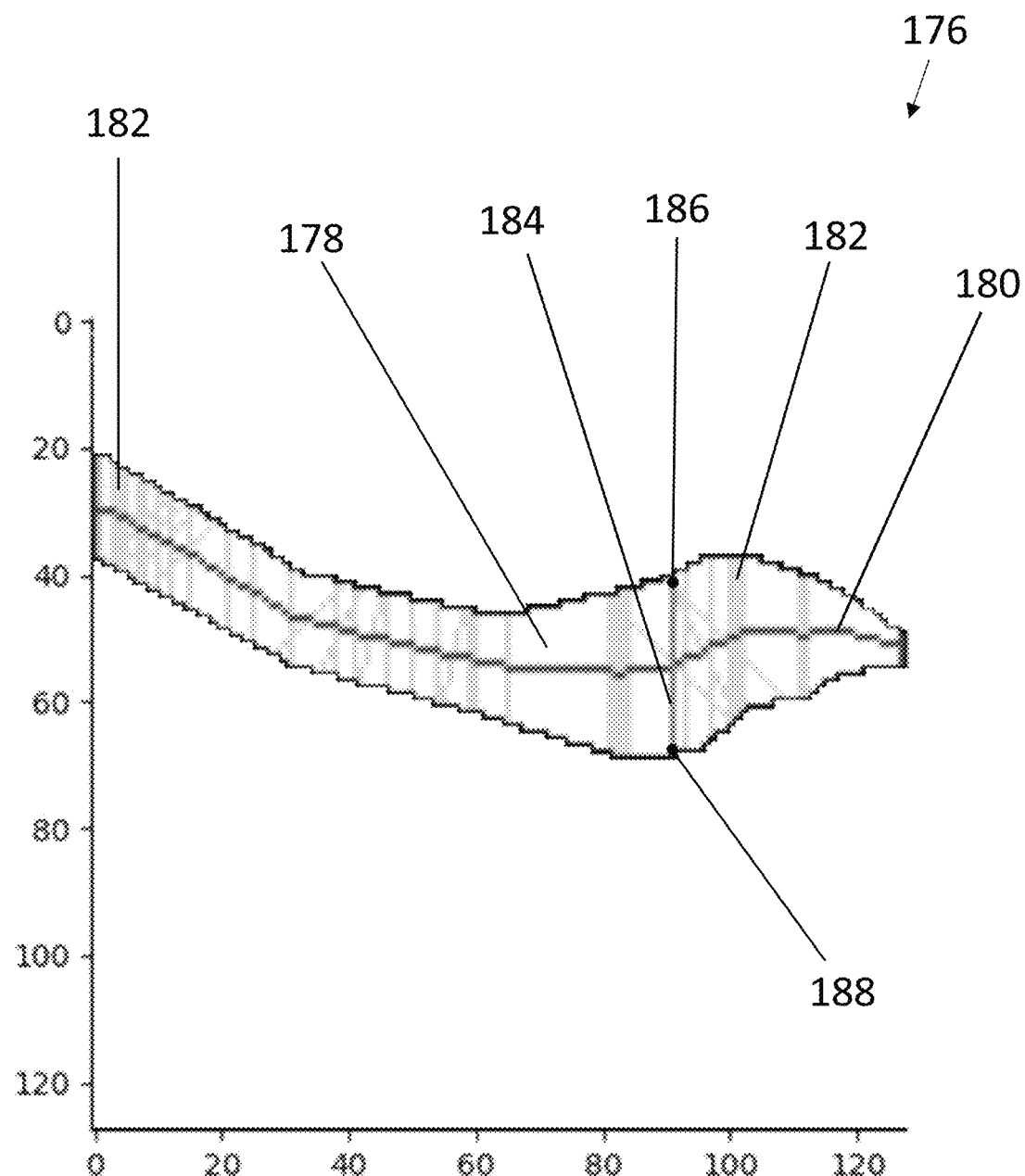
FIG. 11 is a schematic diagram of a segmented tendon image showing a topological skeleton, and perpendicular lines extending therethrough for height/thickness determination, according to an embodiment of the present invention.

Referring to FIG. 5 and additionally with reference to FIG. 11, a flowchart is shown for a method (generally indicated at 122) for calculating the dimensions (e.g., the thickness/height or length) of a corroborated tendon (as in, for example, corroborated from step 120 in FIG. 4) and for automated caliper placement and orientation thereon. Degenerated tendons exhibit decreased mechanical properties, such as stiffness and are generally observed to be disordered with a larger cross-sectional area (CSA), a lower stiffness, and a lower elastic modulus. Changes in the dimensions of tissues are often seen as a sign of injury and degeneration, as an increased area may suggest swelling, inflammation, and general disorder of the tissue so tracking measurements can be critical. Within the scope of the invention, for the purpose of such automatic measurement, without the need for additional user inputs, the corroborated tendon 178 (as shown in FIG. 11) is segmented by the AI model for identification (for example, using methods described in FIG. 4), and its boundaries automatically annotated, at step 115, thus fully defining the tendon boundaries (also referred to as the tendon segmentation mask). At step 116, a topological skeleton of tendon 178 is created. In shape analysis, a skeleton (or topological skeleton) of a shape is a thin version of the tendon that is equidistant to its boundaries. The skeleton may emphasize geometrical and topological properties of the tendon shape, such as its length, height and width. Thereafter, at step 117, a plurality of lines, perpendicular to the topological skeleton, are created, which extend substantially along the entire length of tendon 178. At step 118, the longest of such perpendicular lines is automatically identified and measured, that being the thickest/widest point in tendon 178 (shown in FIG. 11 as 184). Calipers may be auto-placed at points on one or both ends of line 184, such being thickest point for visual identification to a user on a user interface/screen.

The present invention further comprises a method of automatically (without user intervention) placing calipers on boundaries of the corroborated tendon, viewable on a user interface. Such method include the steps of: i) automatically annotating boundaries of the corroborated tendon; and ii) using the annotated boundaries to define automatic caliper placement points. Within the scope of the invention, the automatic measurement tool and automatic caliper placement tool are enabled by the already acquired data (boundaries of the tendon/segmentation mask) created by the AI model in the prior step of probability assessment.

In some embodiments, the method of FIG. 5 may additionally or alternatively be employed to automatically place a Doppler gate or color box on a portion (e.g., the thickest portion) of the tendon. For example, use of a Power Doppler mode in ultrasound imaging of tendons may allow assessment of neovascularization in tendinopathy (forming of blood vessels in tendons).

FIG. 11 represents image 176 of tendon 178 (depicted in a 128*128 scale), to which method 122 of FIG. 5 has been applied. Topological skeleton 180 extends along the length of tendon 178 equidistant to its segmented boundaries and a plurality of perpendicular lines 182 extend along tendon 178 and across topological skeleton 180. The longest perpendicular line is noted as 184 the opposing ends of which (186 and 188) delineate automatic caliper placement points.

Figure 6:
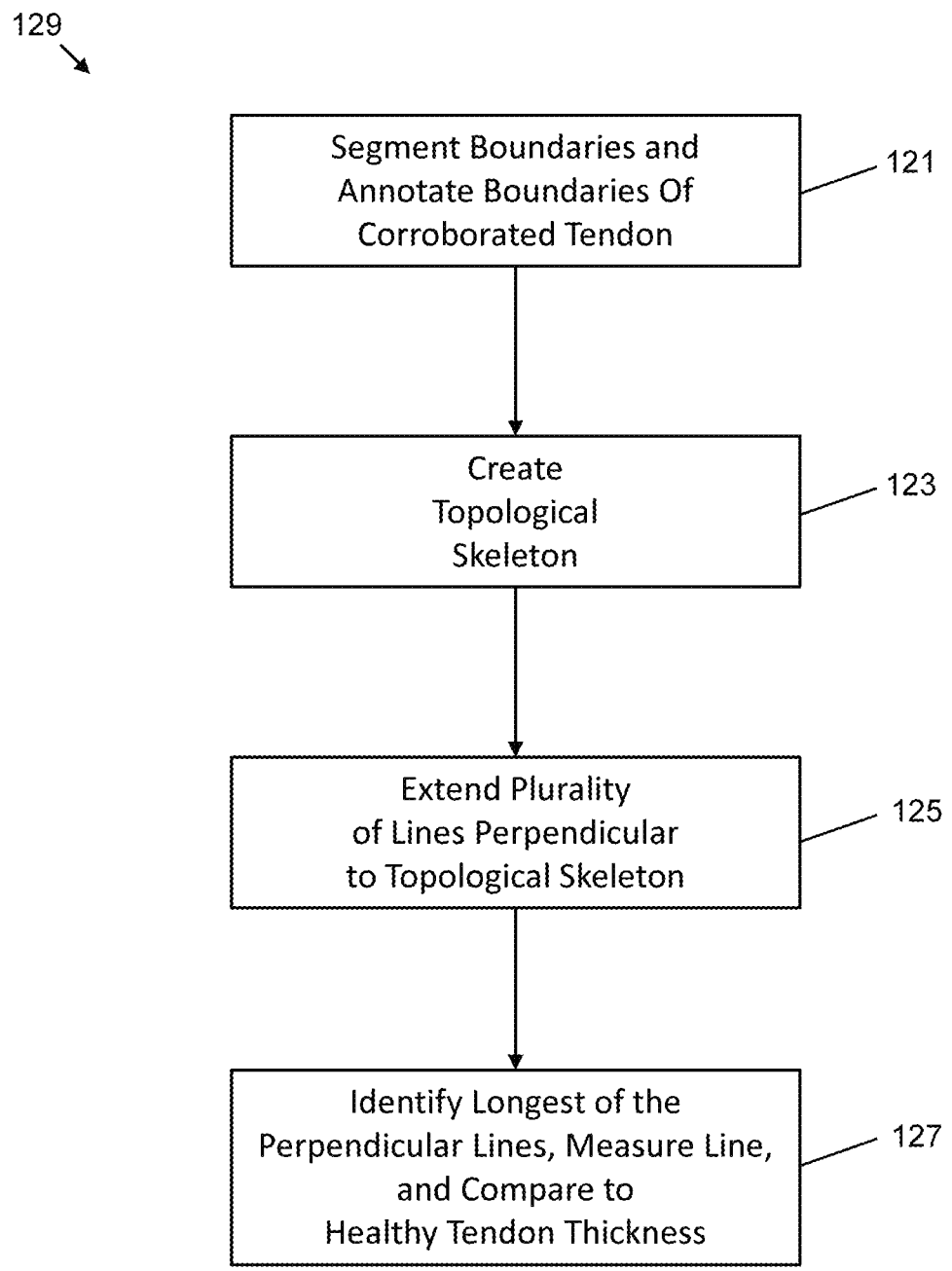
FIG. 6 is a flowchart for annotating boundaries of a selected tendon, thereby to assess damage thereto, according to an embodiment of the present invention.

Referring now to FIG. 6, a flowchart is shown for a method (generally indicated at 129) for assessing a degree of damage to a corroborated tendon (as in, for example, corroborated from step 120 in FIG. 4). Changes in the dimensions of tendon tissues are often seen as a sign of injury and degeneration, as an increased area may suggest swelling, inflammation, and general disorder of the tissue. Within the scope of the invention, for the purpose of such automatic damage assessment, without the need for additional user inputs, the corroborated tendon 178 is segmented by the AI model for identification (for example, using methods described in FIG. 4), and its boundaries automatically annotated, at step 121, thus fully defining the tendon boundaries (also referred to as the tendon segmentation mask). At step 123, a topological skeleton of tendon 178 (as shown in FIG. 11) is created. Thereafter, at step 125, a plurality of lines, perpendicular to the topological skeleton, are created, which extend substantially along the entire length of tendon 178. At step 127, the longest of such perpendicular lines is automatically identified, that being the thickest/widest point in tendon 178 (shown in FIG. 11 as 184). Calipers may be auto-placed at points on both ends of line 184, such being thickest point for visual identification to a user on a user interface/screen. Such caliper placement defines a numerical size for the thickest/widest point in tendon 178. This thickness measurement may be compared to normative standards for a thickness of a particular tendon to determine if follow up assessments and/or treatments are required.

The present invention further provides a method for a user, on a user interface of a display device to adjust the opacity or brightness of the viewable corroborated tendon using for example, a touch-sensitive "slide" module on the display.

Referring to FIG. 7, an exemplary system 130 is shown for identifying a tendon using an AI model and further corroborating its identity by live deployment input(s). The system 130 includes an ultrasound scanner 131 with a processor 132, which is connected to a non-transitory computer readable memory 134 storing computer readable instructions 136, which, when executed by the processor 132, may cause the scanner 131 to provide one or more of the functions of the system 130. Such functions may be, for example, the acquisition of ultrasound data, the processing of ultrasound data, the scan conversion of ultrasound data, the transmission of ultrasound data or ultrasound frames to a display device 150, the detection of operator inputs to the ultrasound scanner 131, and/or the switching of the settings of the ultrasound scanner 131.

Also stored in the computer readable memory 134 may be computer readable data 138, which may be used by the processor 132 in conjunction with the computer readable instructions 136 to provide the functions of the system 130. Computer readable data 138 may include, for example, configuration settings for the scanner 131, such as presets that instruct the processor 132 how to collect and process the ultrasound data for a plurality of tendons and how to acquire a series of ultrasound frames.

The scanner 131 may include an ultrasonic transducer 142 that transmits and receives ultrasound energy in order to acquire ultrasound frames.

The scanner 131 may include a communications module 140 connected to the processor 132. In the illustrated example, the communications module 140 may wirelessly transmit signals to and receive signals from the display device 150 along wireless communication link 144. The protocol used for communications between the scanner 131 and the display device 150 may be WiFi™ or Bluetooth™, for example, or any other suitable two-way radio communications protocol. In some embodiments, the scanner 131 may operate as a WiFi™ hotspot, for example. Communication link 144 may use any suitable wireless communications network connection. In some embodiments, the communication link between the scanner 131 and the display device 150 may be wired. For example, the scanner 131 may be attached to a cord that may be pluggable into a physical port of the display device 150.

In various embodiments, the display device 150 may be, for example, a laptop computer, a tablet computer, a desktop computer, a smart phone, a smart watch, spectacles with a built-in display, a television, a bespoke display or any other display device that is capable of being communicably connected to the scanner 131. The display device 150 may host a screen 152 and may include a processor 154, which may be connected to a non-transitory computer readable memory 156 storing computer readable instructions 158, which, when executed by the processor 154, cause the display device 150 to provide one or more of the functions of the system 130. Such functions may be, for example, the receiving of ultrasound data that may or may not be pre-processed; scan conversion of received ultrasound data into an ultrasound image; processing of ultrasound data in image data frames; the display of a user interface; the control of the scanner 131; the display of an ultrasound image on the screen 152; the processing of a probability of tendon identification (against a tendon-based AI model), the processing in additional inputs to create a corroborated tendon identity; and/or the storage, application, reinforcing and/or training of AI model 10. The screen 152 may comprise a touch-sensitive display (e.g., touchscreen) that can detect a presence of a touch from the operator on screen 152 and can also identify a location of the touch in screen 152. The touch may be applied by, for example, at least one of an individual's hand, glove, stylus, or the like. As such, the touch-sensitive display may be used to receive the at least one "live deployment" input indicating a specific tendon type, of the plurality of different tendon types desired to be scanned (referred to herein as the "selected tendon"). The screen 152 and/or any other user interface may also communicate audibly. The display device 150 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory 156 may be computer readable data 160, which may be used by the processor 154 in conjunction with the computer readable instructions 158 to provide the functions of the system 130. Computer readable data 160 may include, for example, settings for the scanner 131, such as presets for acquiring ultrasound data; settings for a user interface displayed on the screen 152; and/or data for one or more AI models 10 for the processing of a probability of tendon identification (against the tendon-based AI model. Settings may also include any other data that is specific to the way that the scanner 131 operates or that the display device 150 operates.

It can therefore be understood that the computer readable instructions and data used for controlling the system 130 may be located either in the computer readable memory 134 of the scanner 131, the computer readable memory 156 of the display device 150, and/or both the computer readable memories 134, 156.

The display device 150 may also include a communications module 162 connected to the processor 154 for facilitating communication with the scanner 131. In the illustrated example, the communications module 162 wirelessly transmits signals to and receives signals from the scanner 131 on wireless communication link 144. However, as noted, in some embodiments, the connection between scanner 131 and display device 150 may be wired.

Figure 8:
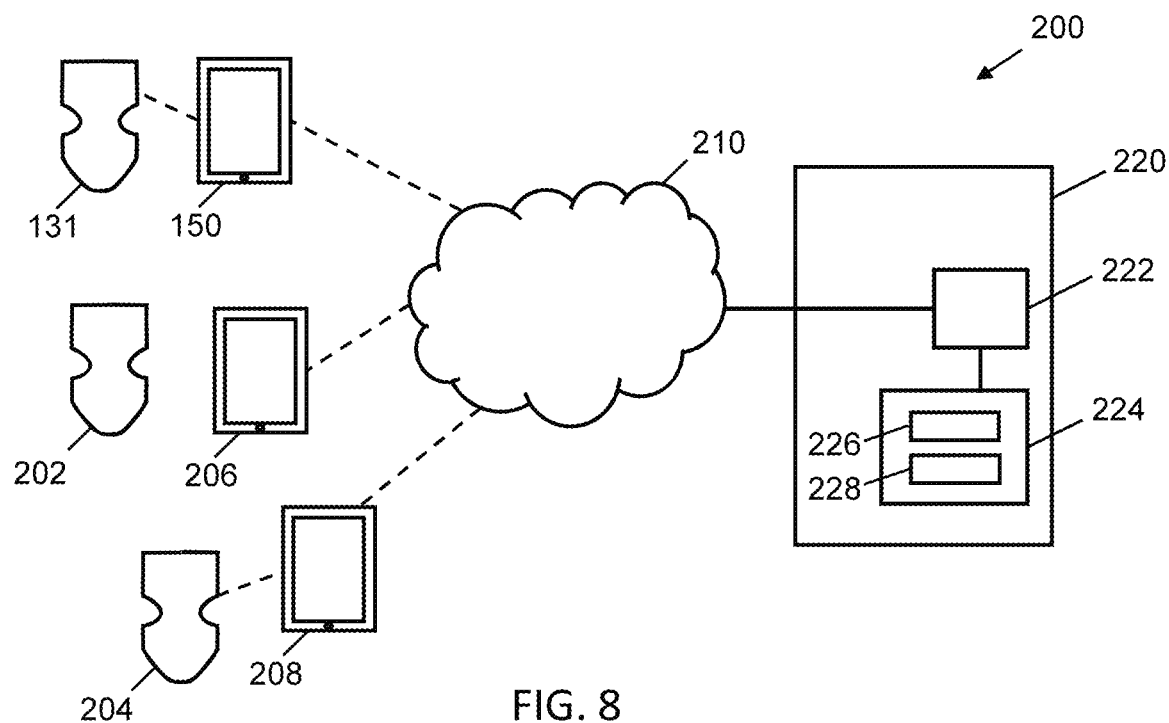
FIG. 8 is a schematic diagram of a system with multiple ultrasound scanners, according to an embodiment of the present invention.

Referring to FIG. 8, a system 200 is shown in which there are multiple similar or different scanners 131, 202, 204 connected to their corresponding display devices 150, 206, 208 and either connected directly, or indirectly via the display devices, to a communications network 210, such as the internet. The scanners 131, 202, 204 may be connected onwards via the communications network 210 to a server 220.

The server 220 may include a processor 222, which may be connected to a non-transitory computer readable memory 224 storing computer readable instructions 226, which, when executed by the processor 222, cause the server 220 to provide one or more of the functions of the system 200. Such functions may be, for example, the receiving of tendon ultrasound frames, the processing of ultrasound data in ultrasound frames, the control of the scanners 131, 202, 204, the processing of a probability of tendon identification (against a tendon-based AI model), the processing of additional inputs to create a corroborated tendon identity, and/or machine learning activities related to one or more AI models 10 (as discussed above in relation to FIGS. 1 and 4).

Also stored in the computer readable memory 224 may be computer readable data 228, which may be used by the processor 222 in conjunction with the computer readable instructions 226 to provide the functions of the system 200. Computer readable data 228 may include, for example, settings for the scanners 131, 202, 204 such as preset parameters for acquiring ultrasound data, settings for user interfaces displayed on the display devices 150, 206, 208, and data for one or more AI models 10. Settings may also include any other data that is specific to the way that the scanners 131, 202, 204 operate or that the display devices 150, 206, 208 operate.

It can therefore be understood that the computer readable instructions and data used for controlling the system 200 may be located either in the computer readable memory of the scanners 131, 202, 204, the computer readable memory of the display devices 150, 206, 208, the computer readable memory 224 of the server 220, or any combination of the foregoing locations.

As noted above, even though the scanners 131, 202, 204 may be different, each tendon ultrasound frame acquired may be used by the AI model 10 for training purposes. Likewise, the tendon ultrasound frames acquired by the individual scanners 131, 202, 204 may all be processed against the AI model 10 for reinforcement of the AI model 10.

In some embodiments, the AI models 10 present in the display devices 150, 206, 208 may be updated from time to time from an AI model 10 present in the server 220, where the AI model present in the server is continually trained using ultrasound frames of additional tendons acquired by multiple scanners 131, 202, 204.

Embodiments of the invention may be implemented using specifically designed hardware, configurable hardware, programmable data processors configured by the provision of software (which may optionally include 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like.

Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, main computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed in parallel or may be performed at different times.

The embodiments may also be provided in the form of a program product. The program product may include any non-transitory medium which carries a set of computer-readable instructions which, when executed by a data processor, cause the data processor to execute a method of the invention. Program products according to the invention may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. software, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments. In some embodiments, the components of the systems and apparatuses may be integrated or separated. Moreover, the operations of the systems and apparatuses disclosed herein may be performed by more, fewer, or other components and the methods described may include more, fewer, or other steps. In other instances, well known elements have not been shown or described in detail and repetitions of steps and features have been omitted to avoid unnecessarily obscuring the invention. Screen shots may show more or less than the examples given herein. Accordingly, the specification is to be regarded in an illustrative, rather than a restrictive, sense.

It is therefore intended that the appended claims and claims hereafter introduced are interpreted to include all such modifications, permutations, additions, omissions and sub-combinations as may reasonably be inferred. The scope of the claims should not be limited by the embodiments set forth in the examples but should be given the broadest interpretation consistent with the description as a whole.

C. Interpretation of Terms

Unless the context clearly requires otherwise, throughout the description and the claims, the following applies:

In general, unless otherwise indicated, singular elements may be in the plural and vice versa with no loss of generality. The use of the masculine can refer to masculine, feminine or both.

The terms "comprise", "comprising" and the like are to be construed in an inclusive sense, as opposed to an exclusive or exhaustive sense, that is to say, in the sense of "including, but not limited to".

The terms "connected", "coupled", or any variant thereof, means any connection or coupling, either direct or indirect, between two or more elements; the coupling or connection between the elements can be physical, logical, or a combination thereof.

The words "herein," "above," "below" and words of similar import, when used in this application, refer to this application as a whole and not to any particular portions of this application.

The word "or" in reference to a list of two or more items covers all of the following interpretations of the word: any of the items in the list, all of the items in the list and any combination of the items in the list.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the examples described and illustrated. The subject matter described herein may assume various alternative orientations. Accordingly, these directional terms are not strictly defined and should not be interpreted narrowly.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

D. Legend of Reference Characters.

| | |
|---|---|
| AI Model | 10 |
| Image (FIG. 9) | 11 |
| Neural Network | 12 |
| First tendon boundary | 13 |

-continued

| D. Legend of Reference Characters. | |
|---|---|
| Training ultrasound frames | 14 |
| Distal side | 15 |
| Second tendon boundary | 17 |
| Proximal side | 19 |
| Tendon frames | 16-38 |
| Acceptable | A |
| Unacceptable | U |
| Preprocessing act | 40 |
| Training step | 42 |
| New ultrasound tendon image | 44 |
| Preprocessing act of new ultrasound image | 46 |
| Stored images for processing through neural network | 48 |
| Probability image | 50 |
| Input(s) | 52 |
| Corroborated tendon type image | 54 |
| Method of FIG. 2 | 55 |
| Methods (specific steps) of training FIG. 2 | 56-71 |
| User interface (FIG. 3) | 72 |
| User interface screen | 74 |
| Training ultrasound image | 76 |
| Cursor | 78 |
| Pull-down menu | 80 |
| Directional arrows | 81 and 83 |
| Enter | 85 |
| Tendon | 82 |
| Tendon options: | 84-100 |
| Achilles | 84 |
| Plantar | 86 |
| Patellar | 88 |
| Rotator | 90 |
| Extensor | 91 |
| Peroneus | 92 |
| Quadricept | 94 |
| Peroneal | 96 |
| Tibialis | 98 |
| Adductor | 100 |
| Points | 102 |
| Lines | 104 |
| Method (generally FIG. 4) | 106 |
| Methods (specific steps) of training FIG. 4 | 108-114 |
| Method (generally FIG. 5) | 122 |
| Methods (specific steps) of training FIG. 5 | 115, 116, 117, 118 |
| Method (generally FIG. 6) | 129 |
| Methods (specific steps) of training FIG. 6 | 121, 123, 125, 127 |
| System (FIG. 7) | 130 |
| Scanner | 131 |
| Process | 132 |
| Memory | 134 |
| Instructions | 136 |
| Computer readable data | 138 |
| Communications module | 140 |
| Ultrasonic transducer | 142 |
| Motor | 143 |
| Communications link | 144 |
| Display device | 150 |
| Screen | 152 |
| Computer readable memory | 156 |
| Computer readable data | 160 |
| Communications module | 162 |
| Image (FIG. 9) | 164 |
| Pixel-1 | 166 |
| Pixel-2 | 168 |
| Pixel-3 | 170 |
| Pixel-4 | 172 |
| Pixel-5 | 174 |
| Image (FIG. 11) | 176 |
| Tendon (FIG. 11) | 178 |
| Topological skeleton | 180 |
| Perpendicular lines | 182 |
| Max. line | 184 |
| First end point of max line | 186 |

-continued

| D. Legend of Reference Characters. | |
|---|---|
| Second end point of max line | 188 |
| System (FIG. 8) | 200 |
| Scanner | 202 |
| Scanner | 204 |
| Display device | 206 |
| Display device | 208 |
| Communications network | 210 |
| Server | 220 |
| Processor | 222 |
| Computer readable memory | 224 |
| Computer readable instructions | 226 |

E. Claim Support

Disclosed herein is a method for identifying a tendon in ultrasound imaging data, the method comprising: deploying an artificial intelligence (AI) model to execute on a computing device, wherein the AI model is trained to identify a plurality of different types of tendons imaged in ultrasound imaging data, and when deployed, the computing device generates a probability for each of the plurality of different types of tendons that the type of tendon is imaged in new ultrasound imaging data; receiving at least one input at the computing device, the at least one input indicating a specific type of the plurality of different types of tendons desired to be scanned (the "selected tendon"); acquiring, at the computing device, the new ultrasound imaging data; processing, using the AI model, the new ultrasound imaging data to generate a degree of probability for each of the plurality of different types of tendons that the type of tendon is imaged in the new ultrasound imaging data; using the at least one input to corroborate the generated degree of probability for a tendon type of the plurality of different types of tendons; and based on such corroboration, determining that the tendon type of the plurality of different types of tendons is imaged in the new ultrasound imaging data (the "corroborated tendon type").

In some embodiments, the method is performed with at least one input comprising a user selection of a preset for the selected tendon.

In some embodiments, a user selection is conveyed at the computing device by at least one of voice command, ultrasound probe gesture or ultrasound input control coupled to a probe.

In some embodiments, the method is performed with at least one input comprising receiving at the computing device optimized imaging parameters, selected from the group consisting of frequency, depth and gain, specific to the selected tendon.

In some embodiments, the at least one input comprises receiving cloud stored data for corroborating the generated degree of probability for the tendon type of the plurality of different types of tendons.

In some embodiments, the plurality of different types of tendons is selected from the group consisting of: Patellar, Plantar fascia, Achilles, Rotator cuff, Extensor, Peroneus, Quadricept, Peroneal, Tibialis, Adductor, Supraspinatus, and Intraspinatus.

In some embodiments, when identifying the plurality of different types of tendons imaged in ultrasound imaging data, the AI model processes the ultrasound imaging data on a per pixel basis, and the probability that a type of tendon of the plurality of different types of tendons is imaged in new ultrasound imaging data is generated on a per pixel basis.

In some embodiments, an output of the AI model for a first pixel of the new ultrasound imaging data is used to corroborate the output of the AI model for a second pixel of the new ultrasound imaging data adjacent to the first pixel.

In some embodiments, when identifying the plurality of different types of tendons imaged in ultrasound image data, the AI model processes the ultrasound imaging data on a line/sample basis, and the probability that a type of tendon of the plurality of different types of tendons is imaged in new ultrasound imaging data is generated on a line/sample basis.

In some embodiments, segmented boundaries of the corroborated tendon type determined to be imaged in the new ultrasound imaging data are automatically annotated and employed to calculate dimensions of the corroborated tendon type.

In some embodiments, segmented boundaries of the corroborated tendon type determined to be imaged in the new ultrasound imaging data are automatically delineated by caliper placement.

In some embodiments, segmented boundaries of the corroborated tendon type determined to be imaged in the new ultrasound imaging data are automatically annotated in the new ultrasound imaging data and employed to assess anomalies and a degree of damage to the corroborated tendon type.

In some embodiments, the corroborated tendon type determined to be imaged in the new ultrasound imaging data is displayed on a user interface with user adjustable opacities.

In some embodiments, ultrasound images are selected from the group consisting of 2D ultrasound images, 3D ultrasound images and 4D ultrasound images.

In some embodiments, additional steps comprise: i) automatically annotating boundaries of the corroborated tendon; ii) using the annotated boundaries to define a topological skeleton, along a length of the corroborated tendon and equidistant to the annotated boundaries; iii) create a plurality of lines perpendicular to the topological skeleton; iv) identify a longest of the plurality of lines (the longest line) which represents the greatest height/thickness of the corroborated tendon.

In some embodiments, the height/thickness of the corroborated tendon is used to identify possible damage to the corroborated tendon.

In some embodiments, the method additionally comprises the steps of: i) automatically annotating boundaries of the corroborated tendon; and ii) using the annotated boundaries to define automatic caliper placement points.

Also disclosed herein is an ultrasound system for identifying a tendon comprising: an ultrasound scanner configured to acquire a plurality of new ultrasound frames; a processor configured to: process each new ultrasound frame of the plurality of new ultrasound frames against an artificial intelligence ("AI") model, wherein said AI model is trained to identify a plurality of different types of tendons imaged in existing ultrasound imaging data, receive at least one input, the at least one input indicating a specific type of the plurality of different types of tendons desired to be scanned (the "selected tendon"); acquire the plurality of new ultrasound frames; generate, using the AI model, a probability for each of the plurality of different types of tendons that the type of tendon imaged in new ultrasound frames is the selected tendon; corroborate, using the at least one input, the generated degree of probability for a tendon type of the plurality of different types of tendons; determine that the tendon type of the plurality of different types of tendons is imaged in the new ultrasound frames (the "corroborated tendon type"); and a display device configured to display at least the corroborated tendon type to a system user.

In some system embodiments, the at least one input comprises a user selection of a preset for the selected tendon.

In some system embodiments, the processor accepts user selection by at least one of voice command, ultrasound probe gesture or ultrasound input control coupled to a probe.

In some embodiments, the processor accepts at least one input which comprises optimized imaging parameters, selected from the group consisting of frequency, depth and gain, specific to the selected tendon.

In some embodiments, the processor accepts at least one input which comprises cloud stored data for corroborating the generated degree of probability for the tendon type of the plurality of different types of tendons.

In some embodiments, the plurality of different types of tendons is selected from the group consisting of: Patellar fascia, Plantar fascia, Achilles, Rotator cuff, Extensor, Peroneus, Quadricept, Peroneal, Tibialis, Adductor, Supraspinatus, and Intraspinatus.

In some embodiments, the processor, employing the AI model, processes data of the ultrasound frames on a per pixel basis, and the probability that a type of tendon of the plurality of different types of tendons is imaged in data from the new ultrasound frames is generated on a per pixel basis.

In some embodiments, the processor employs an output of the AI model for a first pixel of the new ultrasound imaging data to corroborate the output of the AI model for a second pixel of the new ultrasound imaging data adjacent to the first pixel.

In some embodiments, the processor employing the AI model, processes the data of the ultrasound frames on a line/sample basis, and the probability that a type of tendon of the plurality of different types of tendons is imaged in data from the new ultrasound frames is generated on a line/sample basis.

In some embodiments, the processor automatically i) annotates segmented boundaries of the corroborated tendon type determined to be imaged in the new ultrasound frames; and ii) such segmented boundaries are employed to calculate dimensions of the corroborated tendon type.

In some embodiments, the processor automatically delineates caliper placement around segmented boundaries of the corroborated tendon type determined to be imaged in the new ultrasound frames.

In some embodiments, the processor automatically i) annotates segmented boundaries of the corroborated tendon type determined to be imaged in the new ultrasound frames; and ii) assesses anomalies and a degree of damage to the corroborated tendon type.

In some embodiments, the display device comprises a user interface wherein a user, with display of corroborated tendon type determined to be imaged in the new ultrasound frame, may adjust a viewing scale of opacity of such corroborated tendon type.

In some embodiments, the display device is configured to display at least the corroborated tendon type to a system user as ultrasound images selected from the group consisting of 2D ultrasound images, 3D ultrasound images and 4D ultrasound images.

Also disclosed herein is a computer-readable media storing computer-readable instructions, which, when executed by a processor cause the processor to: process each new ultrasound frame of the plurality of new ultrasound frames against an artificial intelligence ("AI") model, wherein said AI model is trained to identify a plurality of different types of tendons imaged in existing ultrasound imaging data, receive at least one input, the at least one input indicating a specific type of the plurality of different types of tendons desired to be scanned (the "selected tendon"); acquire the plurality of new ultrasound frames; generate, using the AI model and the at least one input, a probability for each of the plurality of different types of tendons that the type of tendon imaged in new ultrasound frames is the selected tendon; corroborate, using the at least one input, the generated degree of probability for a tendon type of the plurality of different types of tendons; determine that the tendon type of the plurality of different types of tendons is imaged in the new ultrasound frames (the "corroborated tendon type").

The invention claimed is:

1. A method for identifying a tendon in ultrasound imaging data, the method comprising:
    deploying an artificial intelligence (AI) model to execute on a computing device, wherein the AI model is trained to identify a plurality of different types of tendons imaged in ultrasound imaging data and when deployed, the computing device generates a probability for each of the plurality of different types of tendons that a type of tendon is imaged in new ultrasound imaging data;
    receiving at least one user input at the computing device, the at least one user input indicating a type of the plurality of different types of tendons desired to be scanned, hereinafter, the selected tendon, wherein the at least one user input is selected from the group consisting of i) user selection of a preset comprising the selected tendon; ii) user selection of a workflow comprising the selected tendon; and iii) cloud stored tendon image data;
    acquiring, at the computing device, the new ultrasound imaging data;
    processing, using the AI model, the new ultrasound imaging data to generate a degree of probability for each of the plurality of different types of tendons that the type of tendon is imaged in the new ultrasound imaging data;
    using the at least one user input to corroborate the generated degree of probability for a tendon type of the plurality of different types of tendons; and
    based on the corroboration, determining that the tendon type of the plurality of different types of tendons is imaged in the new ultrasound imaging data, hereinafter, the corroborated tendon type.

2. The method of claim 1 wherein the at least one user input is conveyed at the computing device by at least one of voice command, ultrasound probe gesture or ultrasound input control coupled to a probe.

3. The method of claim 1 wherein the at least one user input additionally comprises receiving at the computing device optimized imaging parameters, selected from the group consisting of frequency, depth and gain, specific to the selected tendon.

4. The method of claim 1 wherein the plurality of different types of tendons is selected from the group consisting of: Patellar, Plantar fascia, Achilles, Rotator cuff, Extensor, Peroneus, Quadricept, Peroneal, Tibialis, Adductor, Supraspinatus, and Intraspinatus.

5. The method of claim 1, wherein when identifying the plurality of different types of tendons imaged in ultrasound imaging data, the AI model processes the ultrasound imaging data on a per pixel basis, and the probability that a type of tendon of the plurality of different types of tendons is imaged in new ultrasound imaging data is generated on a per pixel basis.

6. The method of claim 1 wherein when identifying the plurality of different types of tendons imaged in ultrasound imaging data, the AI model processes the ultrasound imaging data on a per pixel basis, and the probability that a type of tendon of the plurality of different types of tendons is imaged in new ultrasound imaging data is generated on a per pixel basis, and wherein, when deployed, an output of the AI model for a first pixel of the new ultrasound imaging data is used to corroborate the output of the AI model for a second pixel of the new ultrasound imaging data adjacent to the first pixel.

7. The method of claim 1, wherein when identifying the plurality of different types of tendons imaged in ultrasound image data, the AI model processes the ultrasound imaging data on a line/sample basis, and the probability that a type of tendon of the plurality of different types of tendons is imaged in new ultrasound imaging data is generated on a line/sample basis.

8. The method of claim 1 wherein the corroborated tendon type determined to be imaged in the new ultrasound imaging data is displayed on a user interface with user adjustable opacities.

9. The method of claim 1 additionally comprising the steps of: a) automatically identifying and annotating boundaries of the corroborated tendon, forming a segmentation mask of the corroborated tendon; b) using the annotated boundaries to define a topological skeleton, along the corroborated tendon, wherein the topological skeleton is equidistant from each of the annotated boundaries; c) creating a plurality of lines perpendicular to the topological skeleton; and d) identifying a longest line of the plurality of lines, hereinafter the longest line, which represents a greatest height/thickness of the corroborated tendon.

10. The method of claim 9 wherein the height/thickness of the corroborated tendon is used to identify possible damage to the corroborated tendon.

11. An ultrasound system for identifying a tendon comprising:
    an ultrasound scanner configured to acquire a plurality of new ultrasound frames;
    a processor configured to:
        process each new ultrasound frame of the plurality of new ultrasound frames against an artificial intelligence ("AI") model, wherein said AI model is trained to identify a plurality of different types of tendons imaged in existing ultrasound imaging data and to generate a probability for each of the plurality of different types of tendons that a type of tendon is imaged in new ultrasound imaging data;
        receive at least one input, the at least one input indicating a specific type of the plurality of different types of tendons desired to be scanned, hereinafter, the selected tendon wherein the at least one user input is selected from the group consisting of i) user selection of a preset comprising the selected tendon; ii) user selection of a workflow comprising the selected tendon; and iii) cloud stored tendon image data;
        acquire the plurality of new ultrasound frames;
        generate, using the AI model, a degree of probability for each of the plurality of different types of tendons that the type of tendon is imaged in the new ultrasound frames;
        corroborate, using the at least one input, the generated degree of probability for a tendon type of the plurality of different types of tendons;

based on the corroboration, determine that the tendon type of the plurality of different types of tendons is imaged in the new ultrasound frames, hereinafter the corroborated tendon type; and a display device configured to display at least the corroborated tendon type to a system user.

12. The system of claim 11 wherein the plurality of different types of tendons is selected from the group consisting of: Patellar fascia, Plantar fascia, Achilles, Rotator cuff, Extensor, Peroneus, Quadricept, Peroneal, Tibialis, Adductor, Supraspinatus, and Intraspinatus.

13. The system of claim 11, wherein when the processor, employing the AI model, processes data of the ultrasound frames on a per pixel basis, and the probability that a type of tendon of the plurality of different types of tendons is imaged in data from the new ultrasound frames is generated on a per pixel basis.

14. The system of claim 11, wherein the processor employs an output of the AI model for a first pixel of the new ultrasound imaging data to corroborate the output of the AI model for a second pixel of the new ultrasound imaging data adjacent to the first pixel.

15. The system of claim 11, wherein the processor employing the AI model, processes the data of the ultrasound frames on a line/sample basis, and the probability that a type of tendon of the plurality of different types of tendons is imaged in data from the new ultrasound frames is generated on a line/sample basis.

16. The system of claim 11 wherein the processor a) automatically annotates boundaries of the corroborated tendon; b) defines a topological skeleton, along a length of the corroborated tendon and equidistant to the annotated boundaries; c) creates a plurality of lines perpendicular to the topological skeleton; and d) identifies a longest of the plurality of lines (the longest line) which represents the greatest height/thickness of the corroborated tendon.

17. The system of claim 11 wherein the processor automatically annotates segmented boundaries of the corroborated tendon type determined to be imaged in the new ultrasound frames and assesses anomalies and a degree of damage to the corroborated tendon type.

18. A computer-readable media storing computer-readable instructions, which, when executed by a processor cause the processor to:

process each new ultrasound frame of a plurality of new ultrasound frames against an artificial intelligence ("AI") model, wherein said AI model is trained to identify a plurality of different types of tendons imaged in existing ultrasound imaging data and to generate a probability for each of the plurality of different types of tendons that a type of tendon is imaged in new ultrasound imaging frame;

receive at least one input, the at least one input indicating a specific type of the plurality of different types of tendons desired to be scanned, hereinafter the selected tendon, wherein the at least one user input is selected from the group consisting of i) user selection of a preset comprising the selected tendon; ii) user selection of a workflow comprising the selected tendon; and iii) cloud stored tendon image data;

acquire the plurality of new ultrasound frames;

generate, using the AI model a degree of probability for each of the plurality of different types of tendons that the type of tendon is imaged in the new ultrasound frames;

corroborate, using the at least one input, the generated degree of probability for a tendon type of the plurality of different types of tendons; and based on the corroboration, determine that the tendon type of the plurality of different types of tendons is imaged in the new ultrasound frames, hereinafter the corroborated tendon type.

* * * * *